(12) United States Patent
Goradia

(10) Patent No.: US 11,666,367 B2
(45) Date of Patent: Jun. 6, 2023

(54) GUIDANCE APPARATUS FOR IMPLANTATION INTO BONE AND RELATED METHODS OF USE

(71) Applicant: Tushar Goradia, Fair Oaks, CA (US)

(72) Inventor: Tushar Goradia, Fair Oaks, CA (US)

( * ) Notice: Subject to any disclaimer, the term of this patent is extended or adjusted under 35 U.S.C. 154(b) by 312 days.

(21) Appl. No.: 16/427,262

(22) Filed: May 30, 2019

(65) Prior Publication Data
US 2019/0365448 A1 Dec. 5, 2019

Related U.S. Application Data

(60) Provisional application No. 62/678,255, filed on May 30, 2018.

(51) Int. Cl.
| *A61B 17/88* | (2006.01) |
| *A61B 17/86* | (2006.01) |
| *A61B 17/84* | (2006.01) |
| *A61B 17/90* | (2006.01) |

(52) U.S. Cl.
CPC ........ *A61B 17/8872* (2013.01); *A61B 17/848* (2013.01); *A61B 17/864* (2013.01); *A61B 17/8886* (2013.01); *A61B 17/8897* (2013.01); *A61B 17/90* (2021.08)

(58) Field of Classification Search
CPC .............................. A61B 1/8872; A61B 1/8897
See application file for complete search history.

(56) References Cited

U.S. PATENT DOCUMENTS

| 4,790,297 | A | 12/1988 | Luque | |
| 4,907,577 | A | 3/1990 | Wu | |
| 5,024,659 | A | 6/1991 | Sjostrom | |
| 5,720,753 | A * | 2/1998 | Sander | A61B 17/8872 606/104 |
| 7,814,916 | B2 | 10/2010 | Revie et al. | |
| 8,221,427 | B2 | 7/2012 | Roh | |
| 8,285,363 | B2 | 10/2012 | Malackowski et al. | |
| 9,095,395 | B2 * | 8/2015 | Beger | A61B 17/8685 |
| 11,191,583 | B2 * | 12/2021 | Biedermann | A61B 17/864 |
| 2007/0016219 | A1 | 1/2007 | Levine | |
| 2008/0269596 | A1 | 10/2008 | Revie et al. | |
| 2009/0005821 | A1 * | 1/2009 | Chirico | A61B 17/8625 606/319 |

(Continued)

FOREIGN PATENT DOCUMENTS

| CN | 102561665 A | 2/2014 |
| EP | 3323363 A1 | 5/2018 |

(Continued)

OTHER PUBLICATIONS

"O-Arm Surgical Imaging System for Spine, Orthopaedic Trauma, and Neurological Procedures", Medtronic, UC201805459, 2019, 6 pages.

(Continued)

*Primary Examiner* — Nicholas W Woodall
(74) *Attorney, Agent, or Firm* — Fish IP Law, LLP

(57) ABSTRACT

Guiding devices and methods are disclosed that comprise a detachable guide pin. The guiding devices may be driven into a bone to place the detachable guide pin within the bone. Once placed in the bone, the guide pin can be used to guide a surgical device into the bone.

7 Claims, 25 Drawing Sheets

(56) References Cited

U.S. PATENT DOCUMENTS

| | | | |
|---|---|---|---|
| 2009/0187195 A1* | 7/2009 | Berk | A61B 17/22031 606/127 |
| 2011/0054537 A1* | 3/2011 | Miller | A61B 17/1659 606/279 |
| 2011/0301647 A1* | 12/2011 | Hua | A61B 17/8897 606/279 |
| 2012/0022394 A1 | 1/2012 | Wolf, II | |
| 2014/0243602 A1 | 8/2014 | Gorek | |
| 2014/0296928 A1 | 10/2014 | Cheng et al. | |
| 2014/0371756 A1 | 12/2014 | Marigowda | |
| 2015/0127056 A1* | 5/2015 | Roybal | A61B 17/8685 606/279 |
| 2015/0150615 A1 | 6/2015 | Anapliotis | |
| 2016/0113757 A1* | 4/2016 | Diduch | A61B 17/8894 606/104 |
| 2017/0325862 A1* | 11/2017 | Langer | A61B 17/8872 |
| 2018/0008331 A1 | 1/2018 | Roybal | |
| 2019/0191986 A1 | 6/2019 | Genovese et al. | |
| 2019/0209227 A1 | 7/2019 | Tanaka et al. | |

FOREIGN PATENT DOCUMENTS

| | | |
|---|---|---|
| WO | WO2001/010302 A2 | 2/2001 |
| WO | WO2005/084572 A2 | 9/2005 |
| WO | WO2006/039279 A2 | 4/2006 |
| WO | WO2007/035326 A2 | 3/2007 |
| WO | WO2013/185755 A1 | 12/2013 |
| WO | WO2015/054514 A1 | 4/2015 |

OTHER PUBLICATIONS

International Search Report and Written Opinion for PCT/US2019/034747, dated Oct. 4, 2019, 12 pages.

* cited by examiner

GUIDANCE APPARATUS FOR IMPLANTATION INTO BONE AND RELATED METHODS OF USE

This application claims priority to U.S. Provisional Application No. 62/678,255, filed May 30, 2018. All extrinsic materials identified herein are incorporated by reference in their entirety.

FIELD OF THE INVENTION

The field of the invention is medical devices, and more particularly, guiding devices and methods to be used for surgery involving bones.

BACKGROUND

The background description includes information that may be useful in understanding the present invention. It is not an admission that any of the information provided herein is prior art or relevant to the presently claimed invention, or that any publication specifically or implicitly referenced is prior art.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Some types of bone surgery involve insertion of a therapeutic implant into a patient's bone in a specific position. It is helpful to have a guide in place to direct the therapeutic implant since direct visualization of the full trajectory is often obscured by bone or intervening soft tissue.

An example of a guide used to direct an implant is a guide wire. Presently, cannulated pedicle screw systems, which employ a hollow screw, are used to implant pedicle screws into spinal vertebra. A trajectory into the spinal vertebra is created with bone tools introduced using image-guidance technology, and then access to the trajectory is maintained with a guide wire that serves as a track for implantation of the cannulated pedicle screw along the guide wire. Thus, in some prior art systems, a guide wire serves as a guide for a bone implant, and is placed and subsequently withdrawn during the same surgery in which the cannulated pedicle screw is placed.

In another example, U.S. Pat. Pub. 2018/0008331 discloses a modular pedicle screw system that does not require use of a guide wire for implantation. A surgical instrument comprising a cannula and a surgical shaft attached to a first component of the modular pedicle screw are driven into a target area. Once a desired depth is reached, the cannula is removed leaving the first component of the modular pedicle screw and a surgical shaft embedded. The surgical shaft is then used to guide a second component of the modular pedicle screw onto the first component of the modular pedicle screw. Once the second component is placed onto the first component, the surgical shaft is detached from the first component of the modular pedicle screw. The combination of the first and second components forms the final modular pedicle screw.

In yet another example, U.S. Pat. No. 5,024,659 describes a needle guide having a hub and a needle connected to the hub. The needle has a breaking section that allows the needle to break near the hub when the hub is bent back and forth. The needle can be driven into a vertebral disc, and broken once inserted to thereby provide a guide wire for subsequent introduction of a larger cannulated obturator.

Although various systems are described that provide guidance for particular applications, there is still a need for improved guiding devices.

SUMMARY OF THE INVENTION

The inventive subject matter provides apparatus, systems, and methods in which guiding devices are used to place a surgical device into a bone of a patient in a minimally invasive procedure. One contemplated embodiment comprises a guiding device for guiding a hollow surgical device (e.g., pedicle screw, cannulated drill, cannulated tap) into a bone of a patient to a first depth measured from an external surface of the bone into an interior of the bone. The device comprises a rod having a diameter, and a guide pin releasably coupled to a first end of the rod. The guide pin can comprise (i) a tip for inserting the guide pin into the bone to a second depth measured from the external surface of the bone into the interior of the bone, and (ii) a body having a diameter equal to or less than the diameter of the rod. It should be appreciated that the guide pin can be used to subsequently guide a surgical device (e.g., a pedicle screw) into the bone (i) with less imaging guidance than is used in a typical operative procedure to implant the surgical device, and (ii) at a location and date different than the location and date that the guide pin is placed in the bone.

The rod can also comprise a diameter less than 3.5 mm. In some embodiments, the rod and the body of the guide pin have the same diameter. The rod can have a constant diameter between first and second ends of the rod. In other embodiments, the rod comprises a first diameter and a second diameter larger than the first diameter. In such embodiments, the second diameter of the rod can also be larger than the diameter of the body of the guide pin. It should be appreciated that the second diameter is an abrupt diameter change from the first diameter of the rod to thereby create a shoulder that prevents the guiding device to be further driven into the bone. It is contemplated that the larger diameter creating a shoulder can be disposed on the guide pin as opposed to a rod in some embodiments.

The rod and guide pin can be releasably coupled by an intermediate portion that (i) connects the rod and guide pin, and (ii) comprises a diameter that is smaller than a diameter of the rod to thereby allow the intermediate portion to break and separate the rod from the guide pin. Once the guiding device is driven into the bone at a desired depth, the rod could be moved side-to-side relative to the bone or guide pin to cause a break in the intermediate portion, and leave the guide pin implanted in the bone. Typically, the guide pin has a length measured from an end of the tip to an end of the body that is larger than the depth that the guide pin is driven into the bone to thereby allow a portion of the guide pin to extend beyond the external surface of the bone.

In yet another embodiment, a guiding device for guiding a hollow surgical device into a bone of a patient is contemplated. The device comprises a rod having a width, and a guide pin releasably coupled to a first end of the rod. The guide pin can comprise (i) a tip for inserting the guide pin into the bone, and (ii) a body having a width. The rod or guide pin comprises a second width that is greater than each of the width of the rod and the width of the body of the guide pin. It is contemplated that the change between the first width and second width is abrupt to thereby create a shoulder that prevents the guiding device to be further driven into the bone.

The rod and guide pin can be releasably coupled by an intermediate portion that (i) connects the rod and guide pin, and (ii) comprises a diameter that is smaller than a diameter of the rod to thereby allow the intermediate portion to break and separate the rod from the guide pin. Additionally, or alternatively, the guide pin can comprise a non-circular cross section. It is contemplated that the guide pin can comprise a ferromagnetic or radioactive material that allows a user to detect the location of the guide pin with a detection device (e.g., radiation detector, magnetism detector, etc.).

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
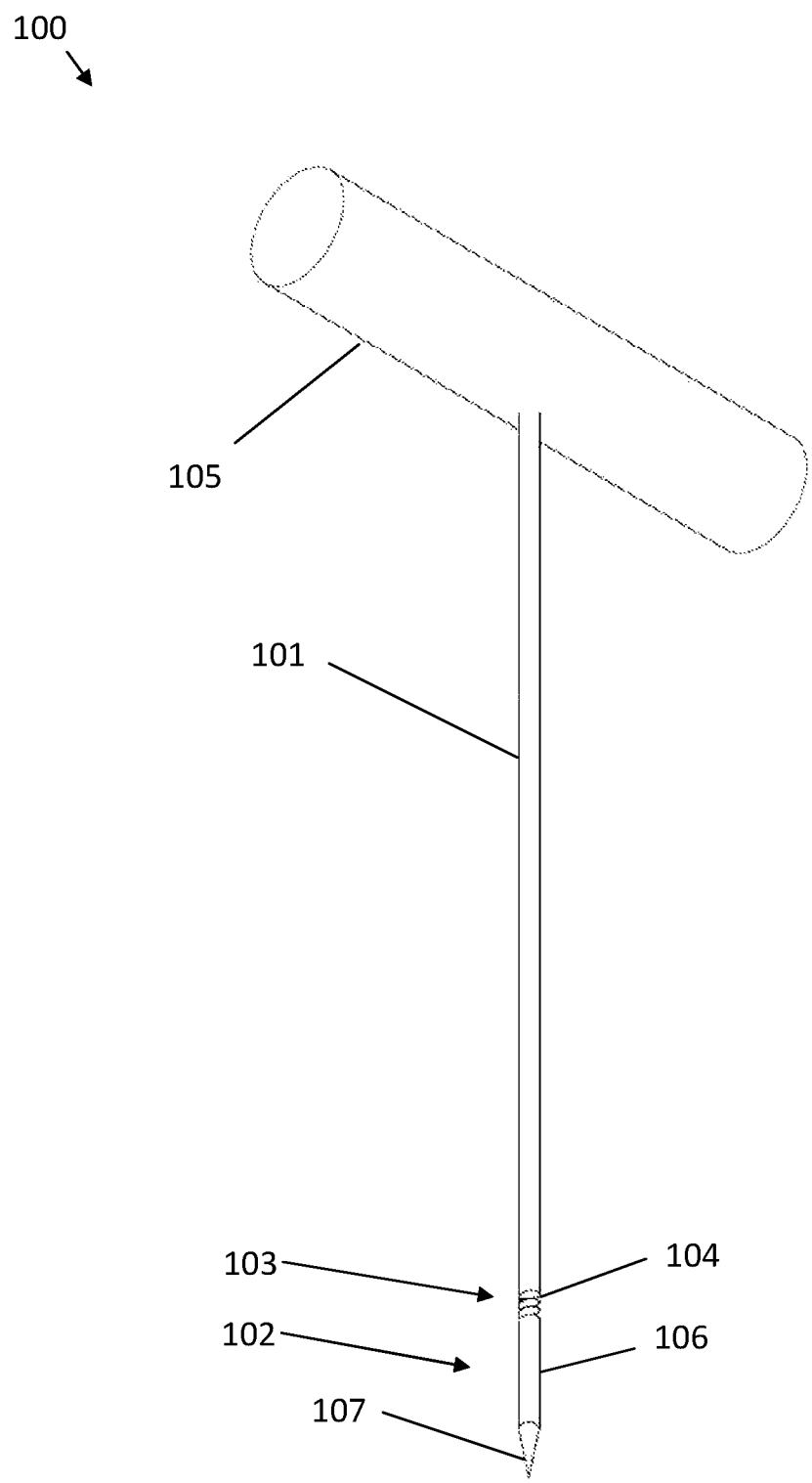
FIG. 1A is a perspective view of an embodiment of a guiding device.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Bone surgery may require insertion of an implant into bone for the therapeutic purpose of repair, stabilization, or modification. Image guidance technology has improved in recent years to facilitate targeted placement of implants. It is common practice to use image guidance technology during the actual implantation surgery. The present invention discloses methods whereby image guidance may predate the definitive surgery for implantation into bone. In one embodiment, a radiologist implants a guide pin of a guidance device into a bone in a radiology suite utilizing image guidance technology, and then on a subsequent day a surgeon implants a bone implant (e.g., pedicle screw) using the guide pin to guide the bone implant in the operating room without the need for image guidance technology. After the bone implant is implanted, the guide pin can be removed or it may remain implanted. It should be appreciated that contemplated guiding devices are sized and dimensioned to be placed within a bone in a minimally invasive procedure.

Contemplated guiding devices can be used to guide various surgical devices into a bone, such as a surgical screw (e.g., a pedicle screw), a cannulated drill, or a cannulated screw tap. One example of a surgical device is a pedicle screw implantation for spinal surgery. Pedicle screws are implanted to help treat some spinal disorders, such as spinal deformity. A pedicle screw may be difficult to insert without image guidance since, in order to avoid the neural elements of the spinal canal, the screw is placed into a narrow corridor of the target spinal vertebra known as the pedicle which lies deep to the visible surface of the target spinal vertebra. Image guidance technologies, such as fluoroscopy, image-guided computer-assisted navigation, computed tomography, and/or robotics serve to provide indirect visualization of this corridor. The use of such equipment in an operating room can be cumbersome and expensive. Many hospitals have a separate fluoroscopy suite or computed tomography suite which allow for some image-guided interventions, but which do not permit open surgical interventions in these suites. Through use of contemplated guiding devices, a guide pin can be implanted in a bone of a patient in a minimally invasive procedure for subsequent use as a guide for the bone implant in an operating room without the need for costly intraoperative image guidance technology.

In the case of pedicle screw implantation, contemplated guiding devices embodiments may be percutaneously driven as a drivable drill bit, bone anchor, trocar, screw, pin, wire, or nail through soft tissue to a target vertebral bone by entering a small incision made in overlying skin. Image guidance can be utilized to direct the guiding device to an implant entry point on the surface of the target bone and toward the pedicle along an acceptable trajectory. Once a portion of the guiding device (e.g., the guide pin) is firmly implanted in the bone, the rod of the guiding device may be released from the guide pin. It is contemplated that the guide pin may be subsequently withdrawn from the patient. It should be appreciated that the guiding device does not require the use of a sleeve or separate cannula for placement of the guide pin into the bone of the patient.

Figure 1B:
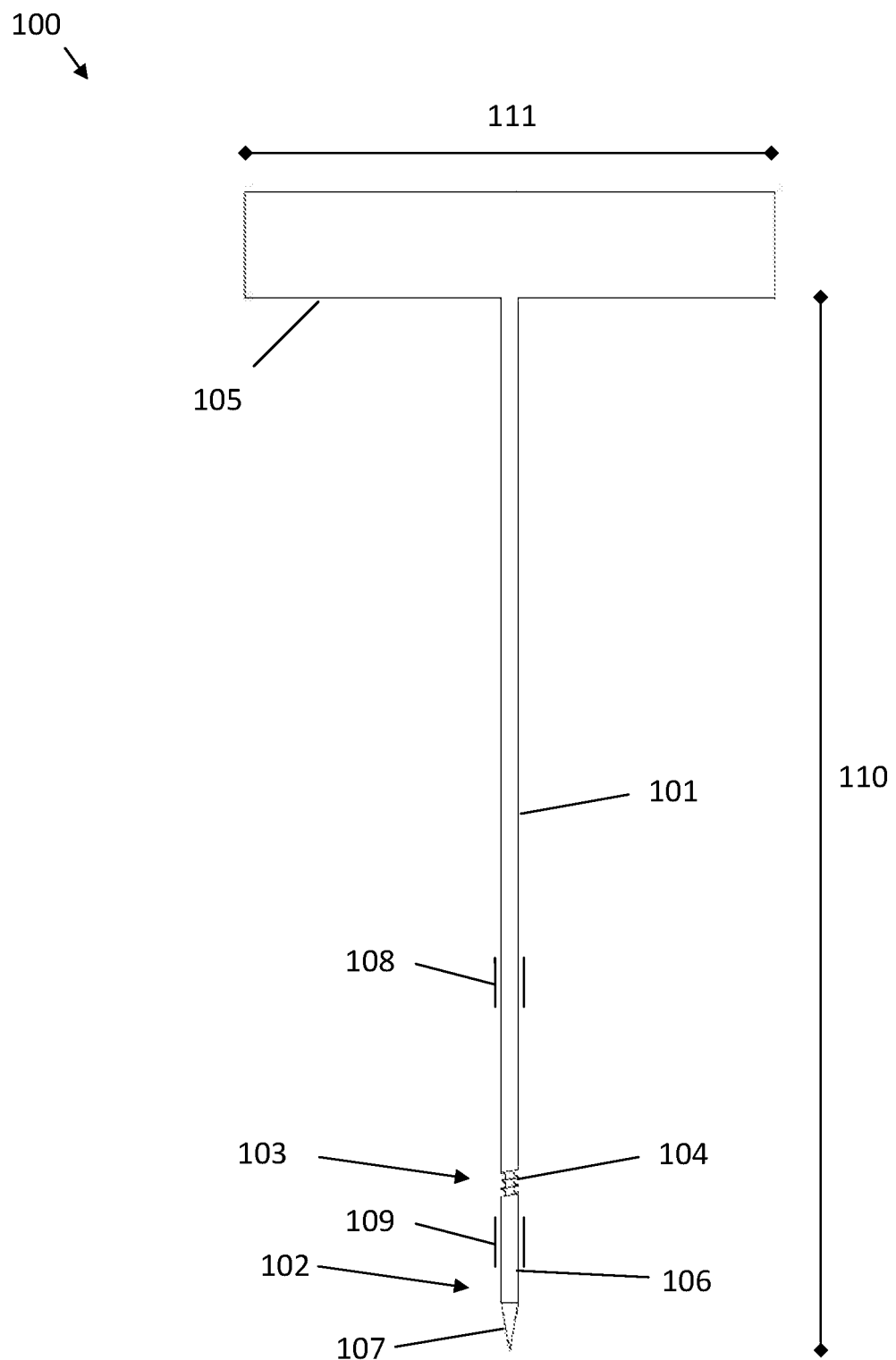
FIG. 1B is a front view of the guiding device of FIG. 1A.

FIGS. 1A-1B show an embodiment of a guiding device 100 that can be used for guiding a hollow surgical device (e.g., surgical screw, cannulated drill, cannulated screw tap, etc.) into a bone of a patient. Guiding device 100 comprises a rod 101 and a guide pin 102 releasably coupled to an end of rod 101. It is contemplated that an intermediate portion 103 connects rod 101 and guide pin 102. Intermediate portion 103 can comprise grooves 104 having a diameter that is smaller than the diameter of rod 101 to thereby allow intermediate portion 103 to break and separate rod 101 from guide pin 102. It is contemplated that a user can intentionally fatigue intermediate portion 103 by repeatedly twisting or bending rod 101 to thereby cause a break in intermediate portion 103. Guiding device 100 can further comprise a handle 105 that facilitates (i) the insertion of guiding device 100 into a bone, and (ii) the twisting or bending action that causes intermediate portion 103 to break and separate rod 101 from guide pin 102. In some embodiments, handle 105 can comprise a width 111 that is greater than an inner diameter of a hollow surgical device, such that handle 105 and rod 101 are removed prior to guiding a surgical device using guide pin 102.

Guide pin 102 comprises a guide body 106 and a tip 107. Tip 107 comprises a sharp end for inserting guide pin 102 into the bone of a patient. Guiding device 100 can be driven into the bone by pushing guiding device 100 through soft biological tissues until it contacts a target bone at a target entry point, and then hammering handle 105 to drive a portion of guide pin 102 into the bone along a planned trajectory utilizing image guidance. Once a desired depth is reached, it is contemplated that grooves 104 of intermediate portion 103 permit breakaway of rod 101 from guide pin 102. It is contemplated that guide pin 102 is in a satisfactory position to serve as a guide for subsequent placement of a surgical device (e.g., therapeutic bone implant). Separation of rod 101 from guide pin 102 can be performed by applying torque to rod 101 while bending the rod 101 after guide pin 102 is seated in bone, or separation can be performed by bending the rod 101 back and forth relative to guide pin 102 to cause a fatigue fracture of intermediate portion 103, which is designed to withstand driving of guiding device 100 into bone but fatigue from repetitive bending or excessive torque.

Rod 101 can comprise a diameter 108 that is constant between first and second ends of rod 101 as shown in FIG. 1B. In some embodiments, diameter 108 can be equal to a diameter 109 of body 106 of guide pin 102. However, it is contemplated that diameter 108 and diameter 109 can be different in other embodiments, such as when diameter 108 is greater than diameter 109 or when diameter 108 is lesser than diameter 109. Diameter 109 can have a diameter equal to or lesser than diameter 108. Suitable dimensions for diameter 108 include between 0.7 and 6.5 mm, between 0.7 and 2 mm, between 1.5 and 6.5 mm, and more typically between 1 and 4 mm. Additionally, or alternatively, diameter 109 can be less than 3.5 mm. Suitable dimensions for diameter 108 include between 0.7 and 6.5 mm, between 0.7 and 2 mm, between 1.5 and 6.5 mm, and more typically between 1 and 4 mm. Additionally, or alternatively, diameter 108 can be less than 3.5 mm. It should be appreciated that diameter 108 and diameter 109 allow guide pin 102 to be implanted into a bone in a minimally invasive procedure when compared to procedures used to implant a surgical device (e.g., pedicle screw).

Guiding device 100 can further comprise a length 110 measured from an end of tip 107 of guide pin 102 to an end of rod 101 opposite the end of tip 107 as shown in FIG. 1B. It is contemplated that length 110 is between 3 and 30 inches. Length 110 at least partially depends on the target bone that will receive guide pin 102 and the age of the patient. In some embodiments, a surgical device is to be implanted into a bone to a first depth measured from an external surface of the bone into an interior of the bone. In such embodiments, tip 107 of guide pin 102 can be driven into the bone to a second depth measured from the external surface of the bone into an interior of the bone. The second depth can be smaller than the first depth, such that the guide pin 102 penetrates the bone at a lesser depth than the surgical device that is subsequently implanted. In other embodiments, the second depth can be equal to or greater than the first depth.

Additionally, or alternatively, guide pin 102 can comprise a length measured from a sharp end of tip 107 to an end of body 106 that is larger than the second depth. This allows a portion of guide pin 102 to extend beyond the surface of the bone for a surgeon to visually locate the target area for implanting a surgical device.

Figure 2A:
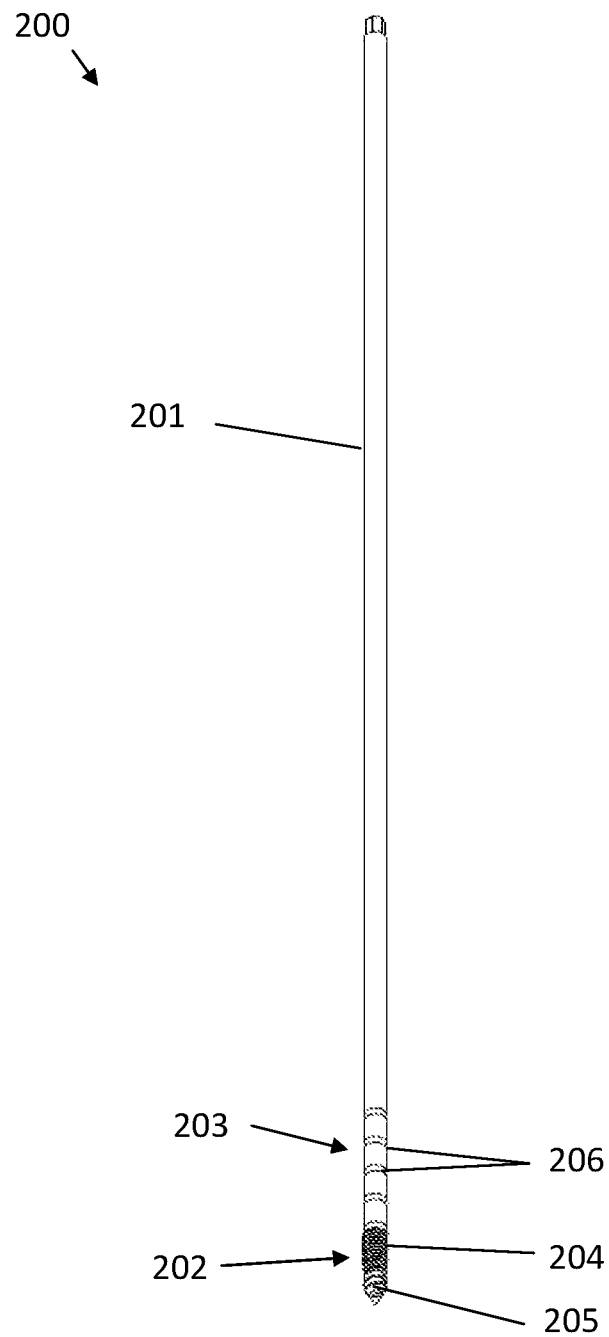
FIG. 2A is a perspective view of another embodiment of a guiding device.
Figure 2B:
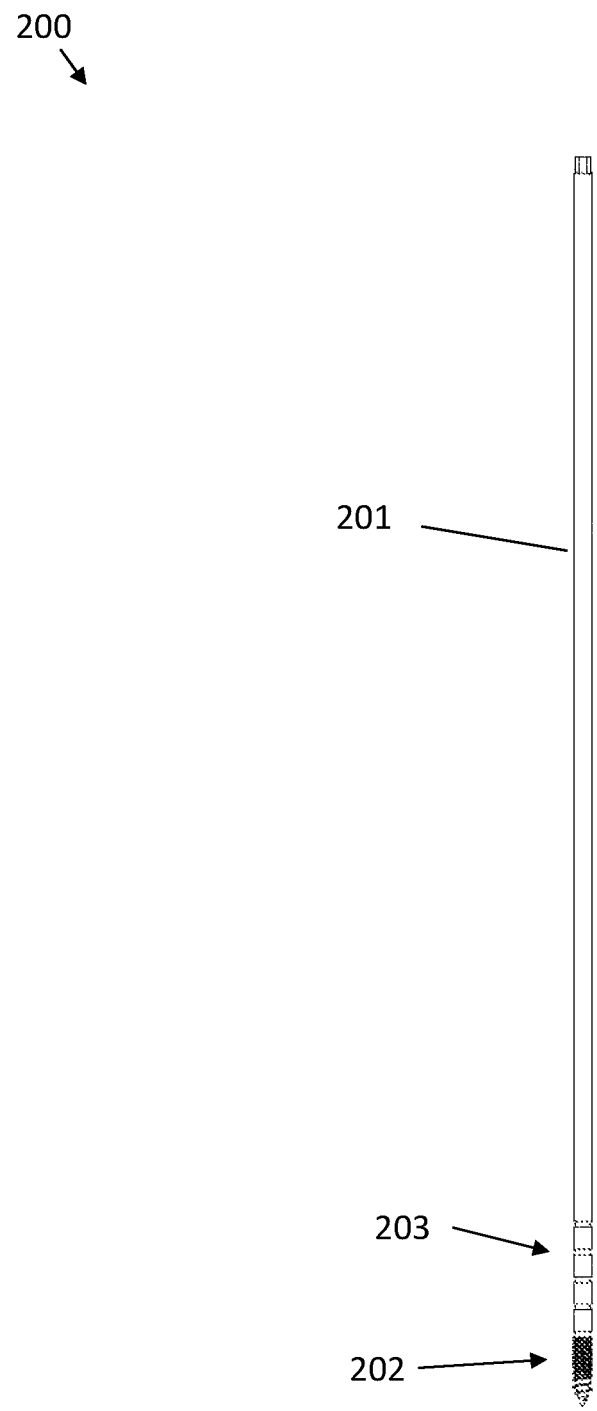
FIG. 2B is a front view of the guiding device of FIG. 2A.

FIGS. 1A-1B show a guide pin 102 that is non-threaded. However, it is contemplated that a guide pin can have threads as shown in FIGS. 2A-2B. FIGS. 2A-2B show a guiding device 200 comprising a rod 201 releasably coupled to a guide pin 202. Guide pin 202 comprises a body 204 and tip 205 having threads. In other embodiments, it is contemplated that only one of body 204 and tip 205 comprises threads.

Guide device 200 is in the form of a drill bit that can be driven into a bone using a drill. Similar to the guiding device 100, guide pin 202 can be separated from rod 201 with back and forth bending of rod 201 relative to a firmly implanted guide pin 202. Guiding device 200 comprises an intermediate portion 203 having a plurality of notches 206 that permits a plurality of options for depth of final placement of the guide pin 202. This allows an operator to act with flexibility in choosing the desired penetration depth of guide pin 202 into the bone. To selectively break intermediate portion 203 at a specific notch 206, an operator drills guide pin 202 to a desired depth that leaves at least one of the plurality of notches 206 protruding from the bone, and breaks rod 201 from guide pin 202 as explained above.

Similar to guiding device 100, guiding device 200 can comprise a rod 201 having a diameter that is constant between first and second ends of rod 201 as shown in FIG. 2B. In some embodiments, the diameter of rod 201 can be equal to the diameter of body 204 of guide pin 202. However, it is contemplated that the diameter of rod 201 and the diameter of body 204 of guide pin 202 can be different in other embodiments, such as when the diameter of rod 201 is greater than the diameter of body 204 of guide pin 202, or when diameter of rod 201 is lesser than the diameter of body 204 of guide pin 202. Suitable dimensions for one or more of the diameters of rod 201 and body 204 of guide pin 202 include between 0.7 and 6.5 mm, between 0.7 and 2 mm, between 1.5 and 6.5 mm, and more typically between 1 and 4 mm. Additionally, or alternatively, one or more of the diameters of rod 201 and body 204 of guide pin 202 can be less than 3.5 mm. Similar to guiding device 100, it should be appreciated that the diameters of rod 201 and body 204 of guide pin 202 allow guide pin 202 to be implanted into a bone in a minimally invasive procedure when compared to procedures used to implant a surgical device (e.g., pedicle screw).

Figure 3:
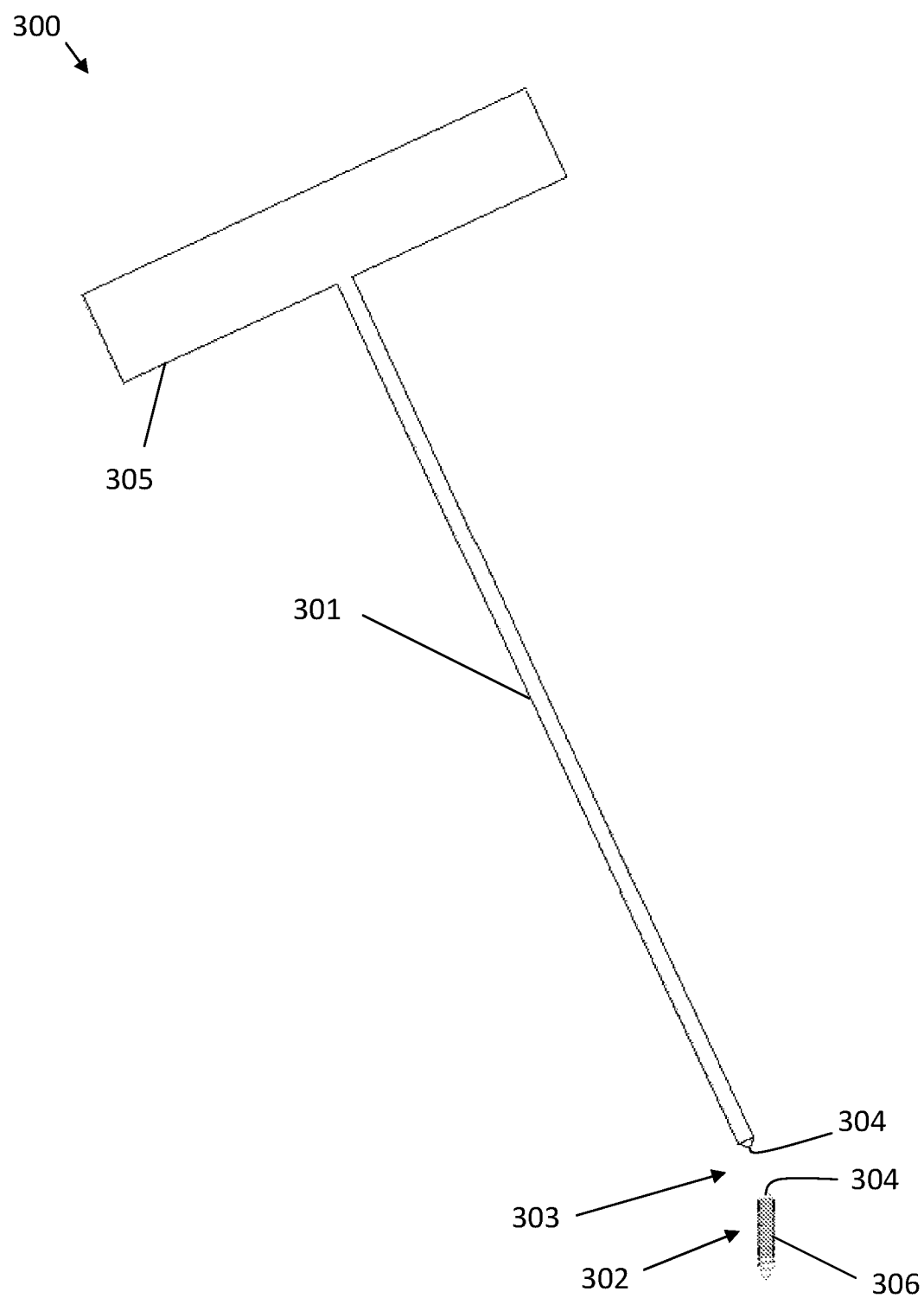
FIG. 3 is a perspective view of another embodiment of a guiding device.

FIG. 3 shows an embodiment of a guidance device 300 having a rod 301 that is detached from a guide pin 302. As explained above, an operator can repeatedly sway rod 301 side to side relative to pin 302 to cause a break in an intermediate portion 303. FIG. 3A shows a break point 304 that is caused in intermediate portion 303. Guiding device 300 comprises a handle 305 that is coupled to rod 301 and is also separated from guide pin 302 when rod 301 is detached from guide pin 302. Guide pin 302 has a body 306 with threads that permit guiding device 300 to be advanced into the bone by rotating handle 305 clockwise. It is contemplated that body 306 of guide pin 302 can have a width that allows threads to mate with internal threads of a surgical device. It is also contemplated that body 306 of guide pin 302 can have a width that is smaller than an internal width of the surgical device, such that a gap is circumferentially disposed between the body 306 of guide pin 302 and the internal surfaces of the surgical device (i.e., body does not mate with internal surfaces of the surgical device to guide the surgical device).

Figure 4:
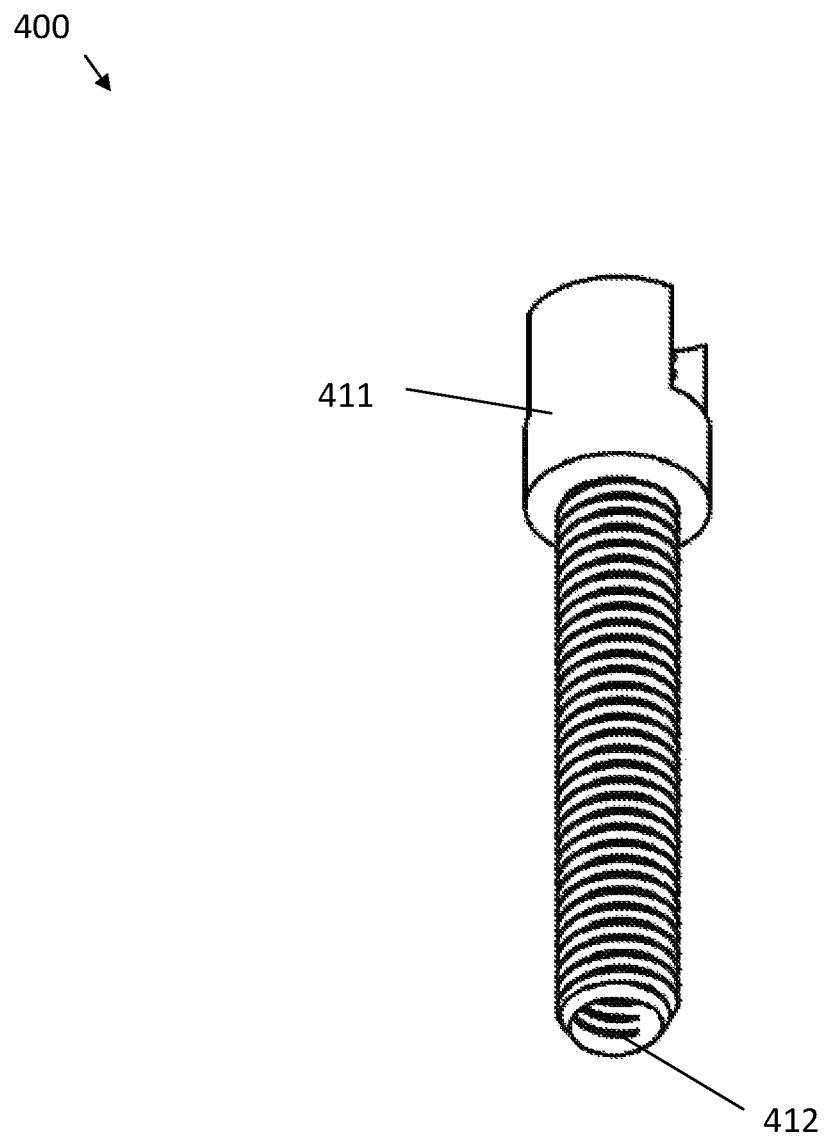
FIG. 4 is a perspective view of an embodiment of a cannulated screw.

FIG. 4 shows an embodiment of a surgical device 400 that can be implanted using the guiding devices (e.g., guiding devices 100, 200, 300, 900, 1000, 1100, etc.) disclosed herein. Surgical device 400 is a cannulated pedicle screw 411 for implantation into a spinal vertebra. Cannulated pedicle screw 411 has a longitudinal inner cavity 412 to permit it to track along the length of a guide pin. Contemplated guide pins can comprise threads that mate with threads in longitudinal inner cavity 412. However, it is also contemplated that a guide pin can comprise a width that is smaller than the width of longitudinal inner cavity 412, such that the guide pin and surfaces of longitudinal inner cavity 412 do not contact one another to mate as the cannulated pedicle screw is implanted into the bone. It should be appreciated that guiding devices can be used to guide other surgical devices into a bone, such as bone fracture fixation screws (e.g., for hip fractures, humerus fractures, tibial fractures), a cannulated drill, a cannulated screw tap, or any other surgical device through a bone so long as it has a structure that allows the surgical device (e.g., hollow opening, cavity, etc.) to be implanted over a guide pin of contemplated guiding devices. Additionally, or alternatively, contemplated guide pins can be used to direct catheters through bones to a specific target.

Figure 5:
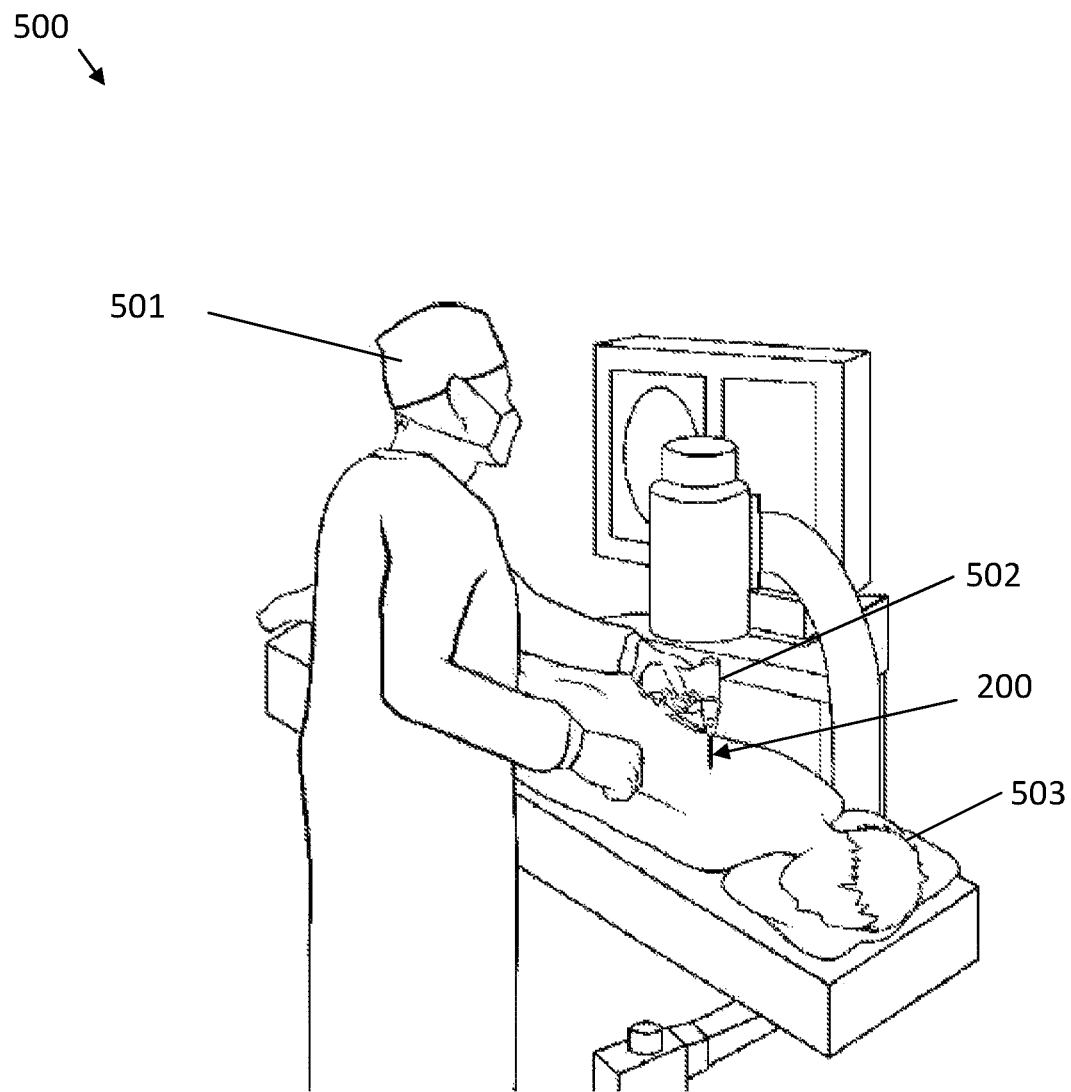
FIG. 5 is an illustration of the guiding device of FIGS. 2A-2B being used in a drill in a radiology suite.

FIG. 5 shows a radiologist 501 in a radiology suite 500 using a drill 502 to place guiding device 200 in the spine of a patient 503.

FIGS. 6A-6G illustrate the successive steps of a method of using guiding device 300 to place the hollow surgical device 400 into a spinal vertebra 720 of a patient.

Figure 6A:
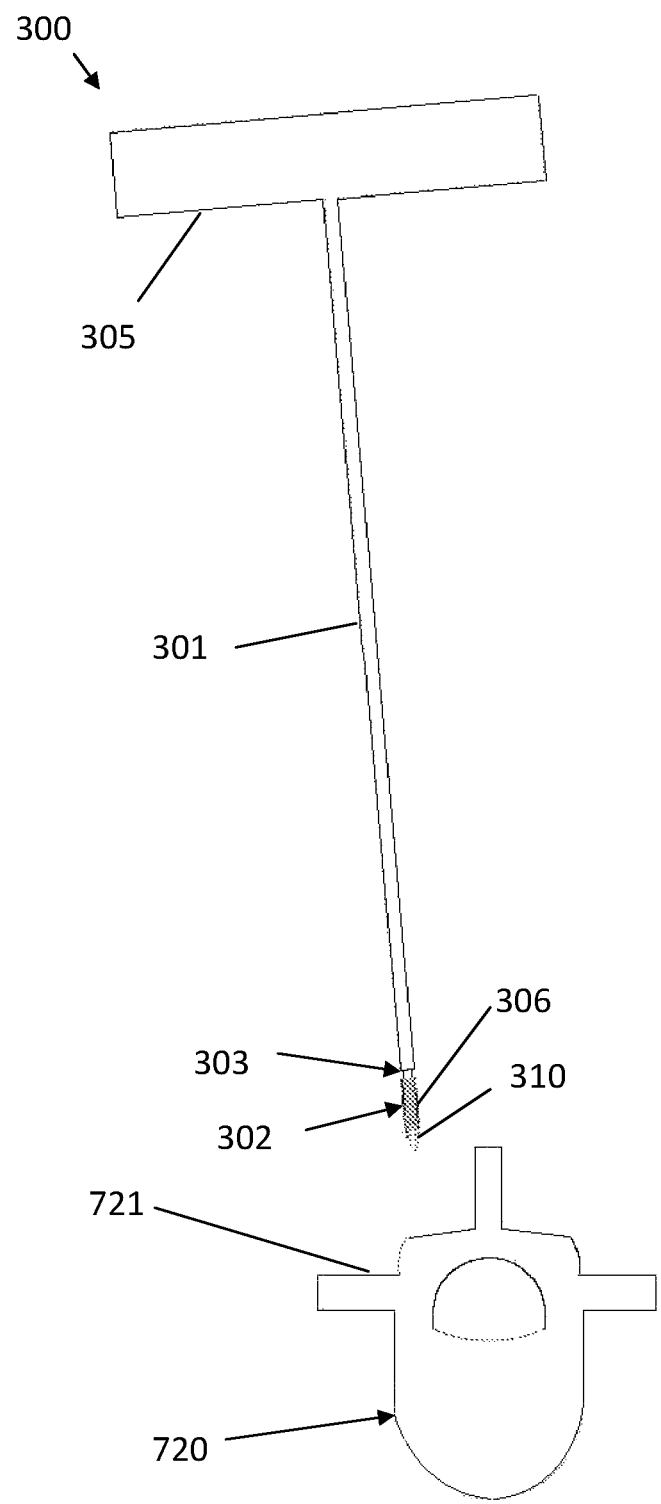
FIG. 6A is an illustration of an embodiment of the guiding device of FIG. 3 as it approaches a spinal vertebra.

FIG. 6A is an illustration of guiding device 300 as it is being introduced towards a spinal vertebra 720. Prior to this step, the radiologist, nurse, or surgeon prepares the treatment area with a local anesthetic on the patient's back and makes a small incision over the spinal vertebra 720. One advantage of the guiding device 300 and its method of use is that only a very small incision is required, preferably 1 inch and more preferably less than ½ an inch.

As described above, guiding device 300 has rod 301 and guide pin 302, with a singly grooved breakable intermediate portion 303 disposed between them. The tip 310 comprises a sharp end that is used to penetrate the lamina 721 of the spinal vertebra 720 by hammering the handle 305 along the long axis of the guiding device 300. Since guiding device 300 does not have a safety stop (e.g., widened portion 1109 in FIG. 11A), gradual advancement of the tip 310 can be accomplished using image guidance.

Figure 6B:
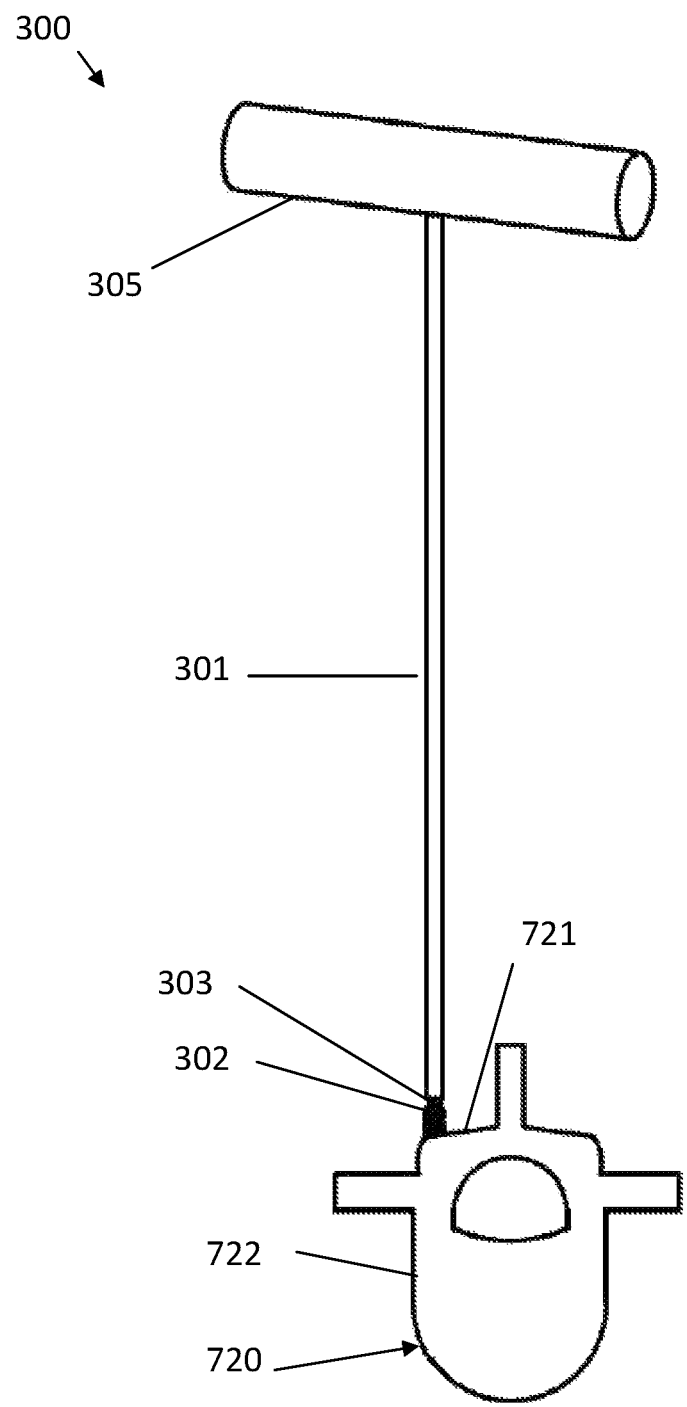
FIG. 6B is an illustration of the guiding device of FIG. 3 as it is placed into the spinal vertebra.

FIG. 6B is an illustration of the guiding device 300 after tip 310 of guide pin 302 is seated into the spinal vertebra 720 and then advanced by rotating the handle 305 clockwise to screw the helical screw threads of guide pin 302 into the lamina 721 towards the pedicle 722 using image guidance (not shown).

Figure 6C:
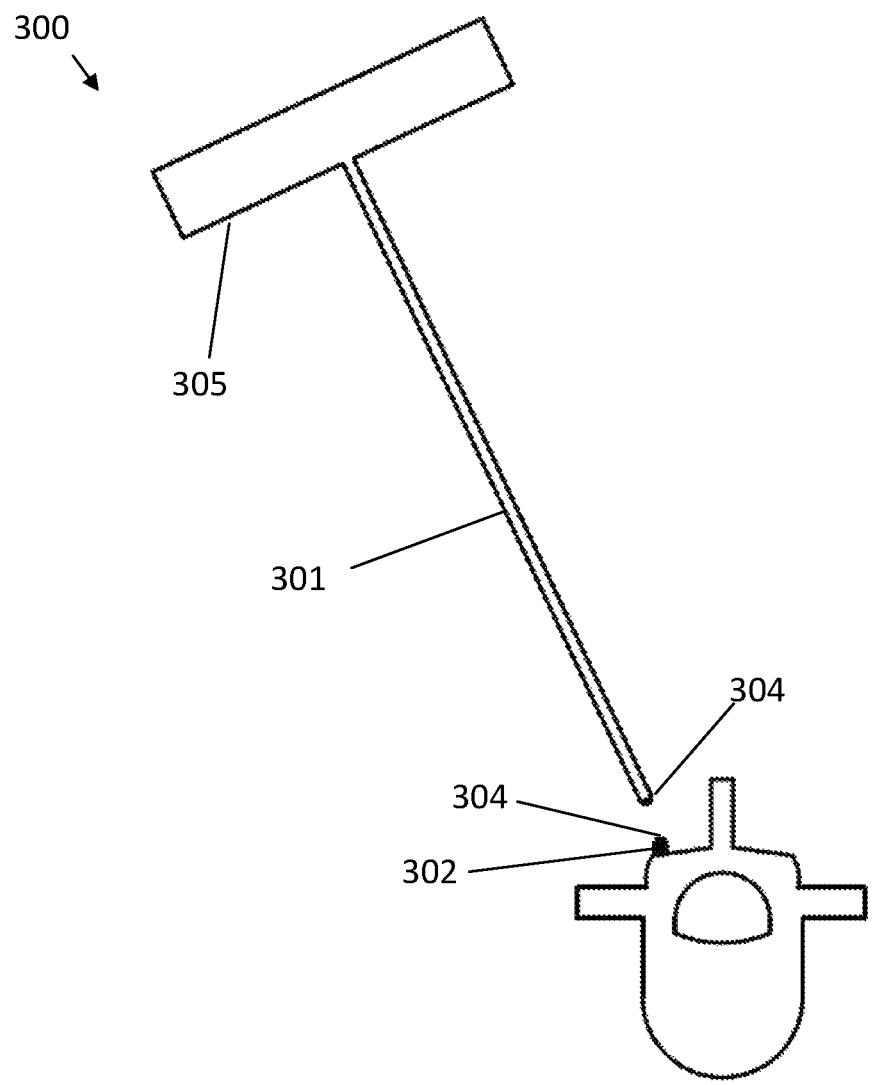
FIG. 6C is an illustration of the guiding device of FIG. 3 after the guide pin is detached from the rod.

FIG. 6C is an illustration of the guiding device 300 after it has been manipulated to cause breakage of the intermediate portion 303 thereby releasing the rod 301 from the guide pin 302.

Figure 6D:
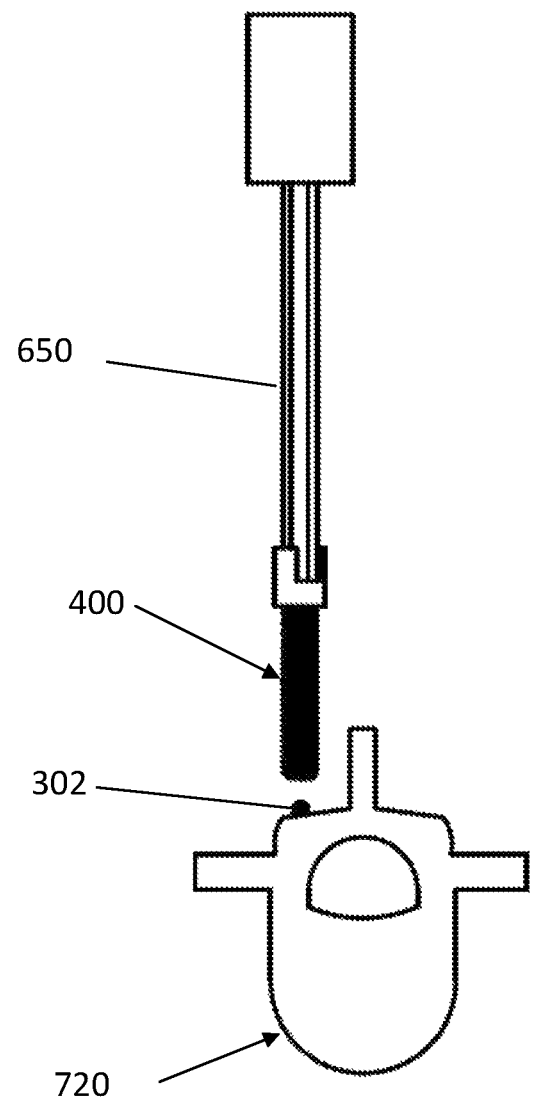
FIG. 6D is an illustration of an embodiment of a cannulated screw as it approaches the spinal vertebra.

FIG. 6D is an illustration of the introduction of the hollow surgical device 400 being held by a screwdriver 650 during initial approach to the spinal vertebra 720 in which the guide pin 302 of the guiding device 300 is already positioned to guide the hollow surgical device 400. During this step, a radiologist or surgeon visually confirms the location of the guide pin 302 as opposed to relying on x-ray imaging for proper placement. However, it is contemplated that the radiologist or surgeon could confirm location of the guide pin 302 using magnetism and/or x-ray imaging to facilitate placement of the hollow surgical device 400 over guide pin 302.

Once the guide pin 302 is located, a hollow surgical device 400 is slowly inserted on top of the guide pin 302 by applying gentle force. The appropriate insertion of the hollow surgical device 400 over the guide pin 302 is unencumbered because the inner cannula of the hollow surgical device 400 is wider than the diameter of the guide pin 302, and thus the guide pin 302 helps direct placement of the hollow surgical device 400 along a path of lesser resistance that is collinear with the long axis of the guide pin 302. An increase resistance during the advancement process is an indication of deviation of the trajectory of the hollow surgical device 400 from its planned path, and by detecting such resistance a surgeon can modify angulation of the hollow surgical device 400 to follow the track that is provided by the guide pin 302.

Figure 6E:
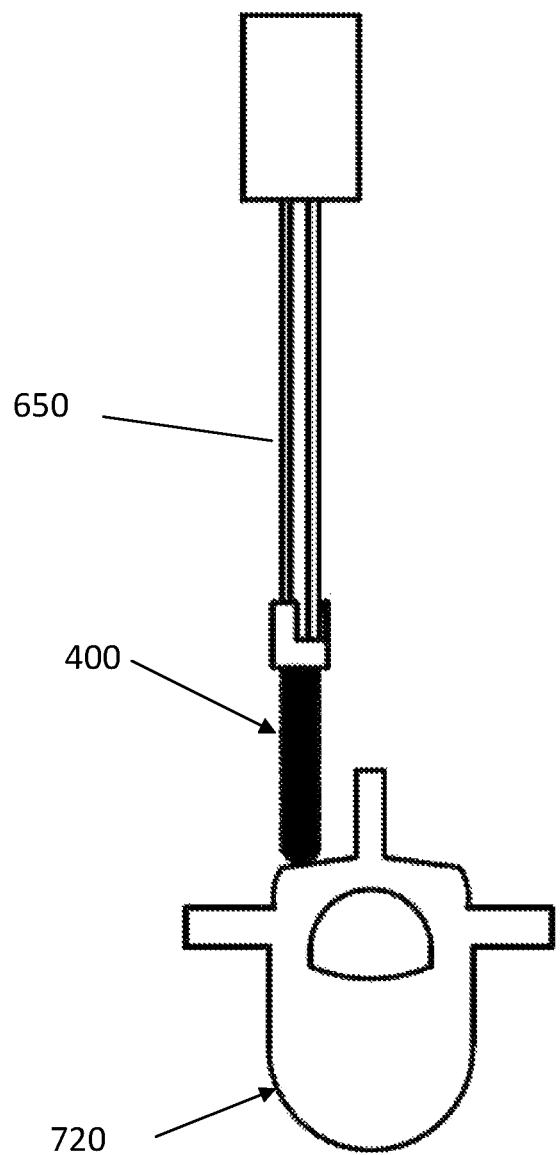
FIG. 6E is an illustration of the cannulated screw of FIG. 6D as it is driven into the spinal vertebra using the guide pin of the guiding device of FIG. 3 as a guide.

FIG. 6E is an illustration of initial capture of the guide pin 302 of the guiding device 300 by the hollow surgical device 400.

Figure 6F:
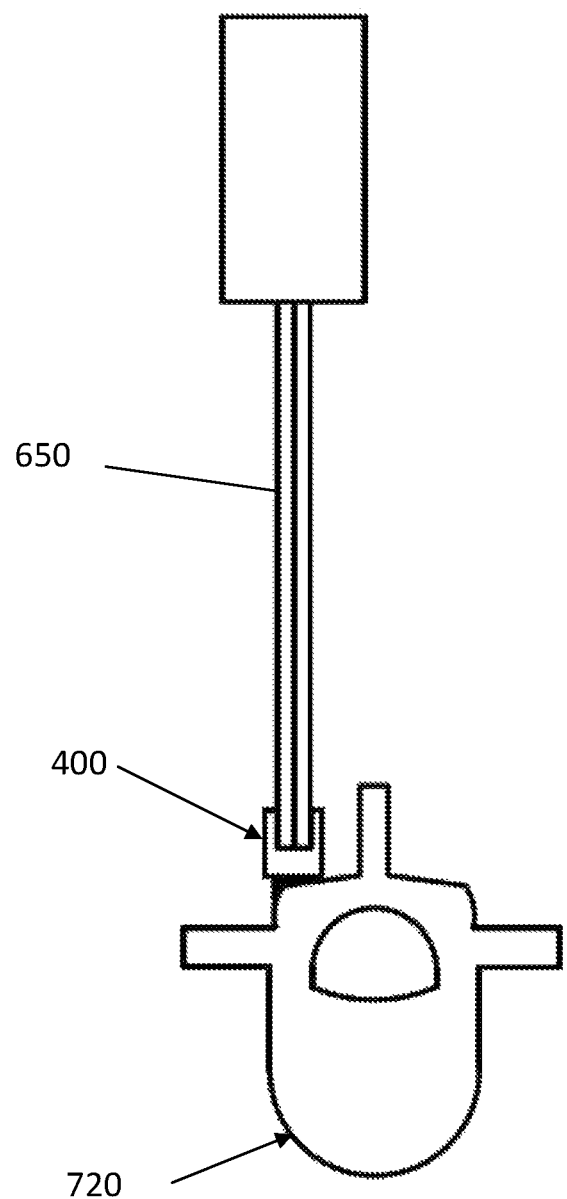
FIG. 6F is an illustration of the cannulated screw of FIG. 6D fully driven into the spinal vertebra.

FIG. 6F is an illustration of final insertion of the hollow surgical device 400 into the spinal vertebra 720 while the hollow surgical device 400 is attached to the screwdriver 650. At this stage, the radiologist or surgeon can continue to screw the hollow surgical device 400 onto the threads of body 306 of guide pin 302 until fully implanted.

Figure 6G:
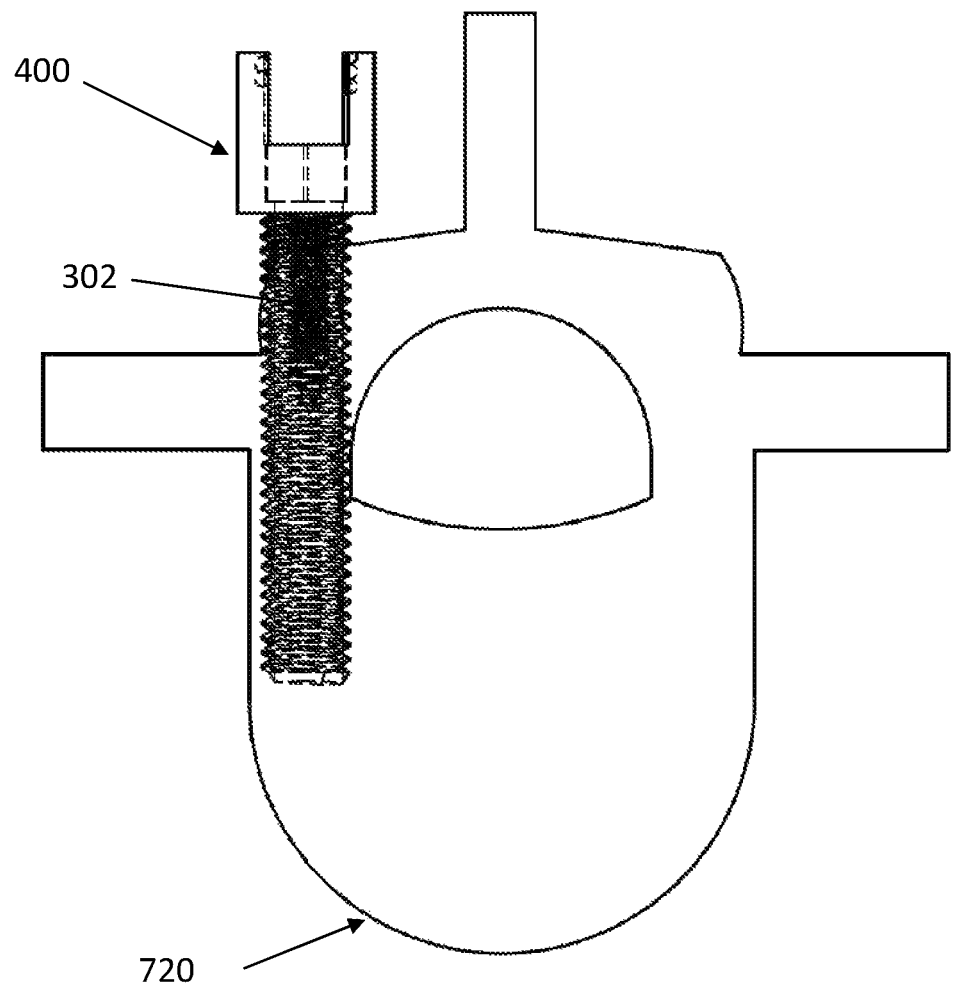
FIG. 6G is a hidden line view of the final placement of the cannulated screw in FIG. 6D and the guide pin of the guiding device of FIG. 3.

FIG. 6G is a hidden line frontal view of final placement of the hollow surgical device 400, which has been implanted by screwing it in over the guide pin 302. As shown in FIG. 6G, the width of guide pin 302 is smaller than the width of the internal cavity of surgical device 400 to thereby leave a gap between guide pin 302 and surgical device 400. In other embodiments, it is contemplated that guide pin 302 can have threads that mate with threads of a surgical device as it is driven into the bone.

There are 3 key parameters for proper placement of the hollow surgical device 400: (1) entry point, (2) linear trajectory, and (3) depth. The guide pin 302 provides the entry point and linear trajectory, even when the guide pin 302 is much shorter than the hollow surgical device 400. The guide pin 302 is preferably deep enough into the spinal vertebra 720 such that it is unlikely to dislodge. In some applications, it is estimated that about 5-20 mm would be an adequate depth for the guide pin 302. The third key parameter (i.e., depth of the screw), is pre-planned based on pre-operative CT scans. For pedicle screws the depth of the screw is typically about 30-55 mm.

One advantage of the method of using guiding device 300 as shown in FIGS. 6A-6G is that it is minimally invasive and requires a much smaller incision than conventional procedures and devices. The methods and devices contemplated herein eliminate the need for additional steps required by other procedures, including: (1) driving a K-wire to the proposed entry point in the bone; (2) taking multiple x-rays to verify a good entry point; (3) driving the K-wire further along an acceptable trajectory within the bone; (4) taking multiple x-rays to verify that the K-wire is along a good trajectory; (5) passing a cannulated screw over the K-wire and screwing the screw in place; and (6) withdrawing the K-wire.

By eliminating the need for x-ray imaging during surgery, the methods and devices contemplated herein can be done under local anesthesia. In contrast, traditional methods that require the surgeon to "open the patient up" with a larger incision, and then place the guide wire using imaging, significantly increases the patient's time under general anesthesia.

Figure 7:
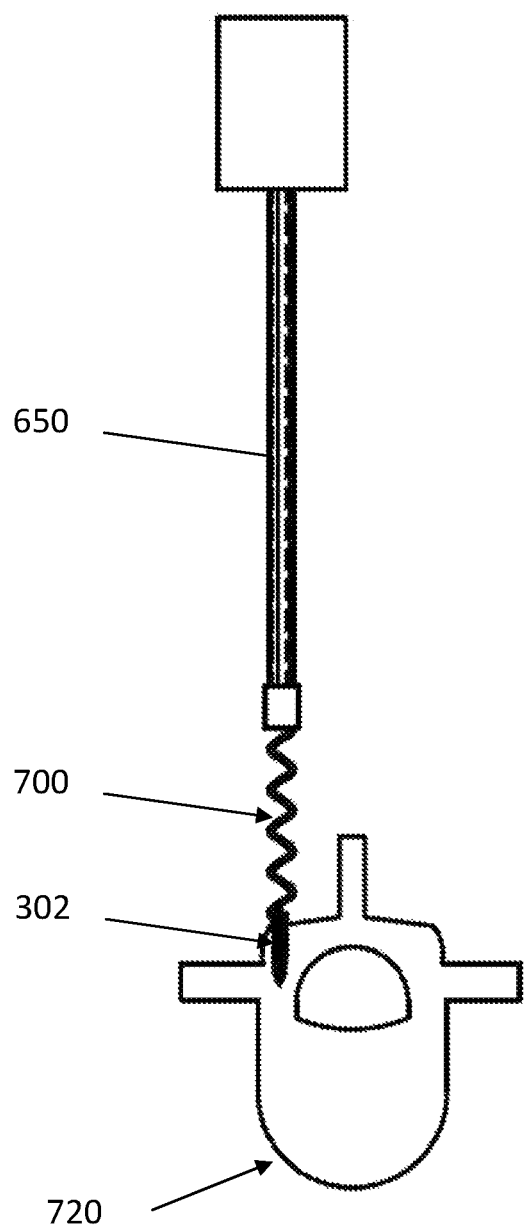
FIG. 7 is a hidden line view of another embodiment of a guiding device as it is driven into the spinal vertebra using the guide pin of the guiding device of FIG. 3 as a guide.

FIG. 7 is a hidden line frontal view of the capture of the guide pin 302 of the guiding device 300 by a helical surgical device 700 which is to be implanted in spinal vertebra 720 using screwdriver 650. The helical device 700 is an alternative embodiment of a type of pedicle screw and is essentially a corkscrew pedicle screw. A corkscrew (or spiral) pedicle screw provides enhanced bone purchase compared to a traditional pedicle screw with a shank (e.g., hollow surgical device 400), and can be used in patients with poor bone quality.

Figure 8:
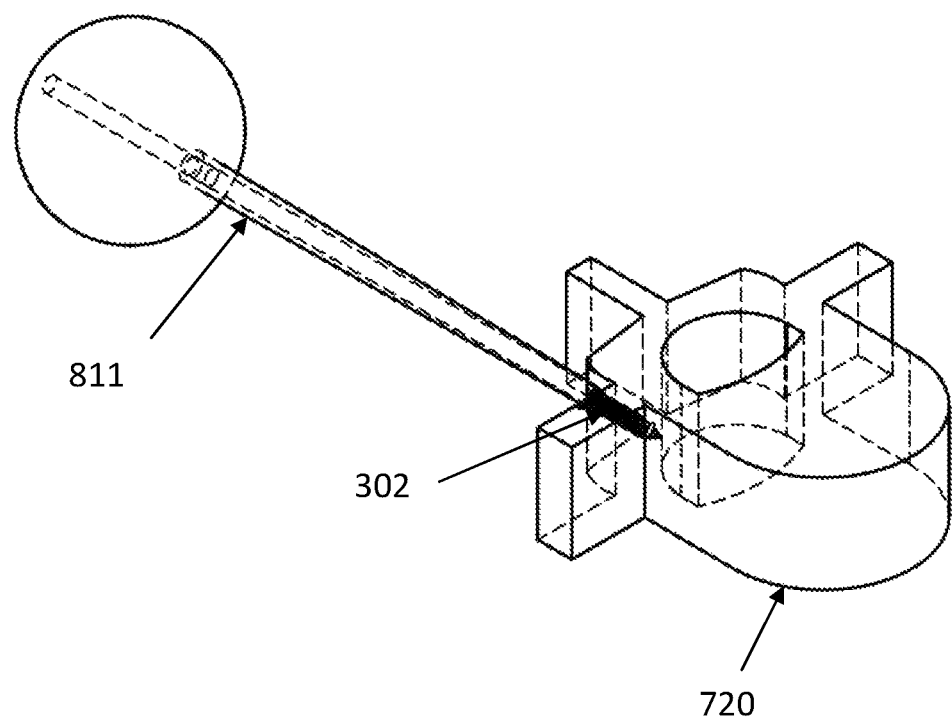
FIG. 8 is a hidden line view of an embodiment of a guiding device being used to guide a cannulated bone probe.

FIG. 8 is a hidden line perspective view of the guide pin 302 of guiding device 300 being used to guide a cannulated bone probe 811. In this case, the guide pin 302 is used with the cannulated bone probe 811 to help excavate the trajectory for placement of a pedicle screw. When using this method, after excavation of the path for the pedicle screw, the guide pin 302 is removed and a non-cannulated screw can be inserted by gently screwing the screw into the space developed for its placement.

Figure 9A:
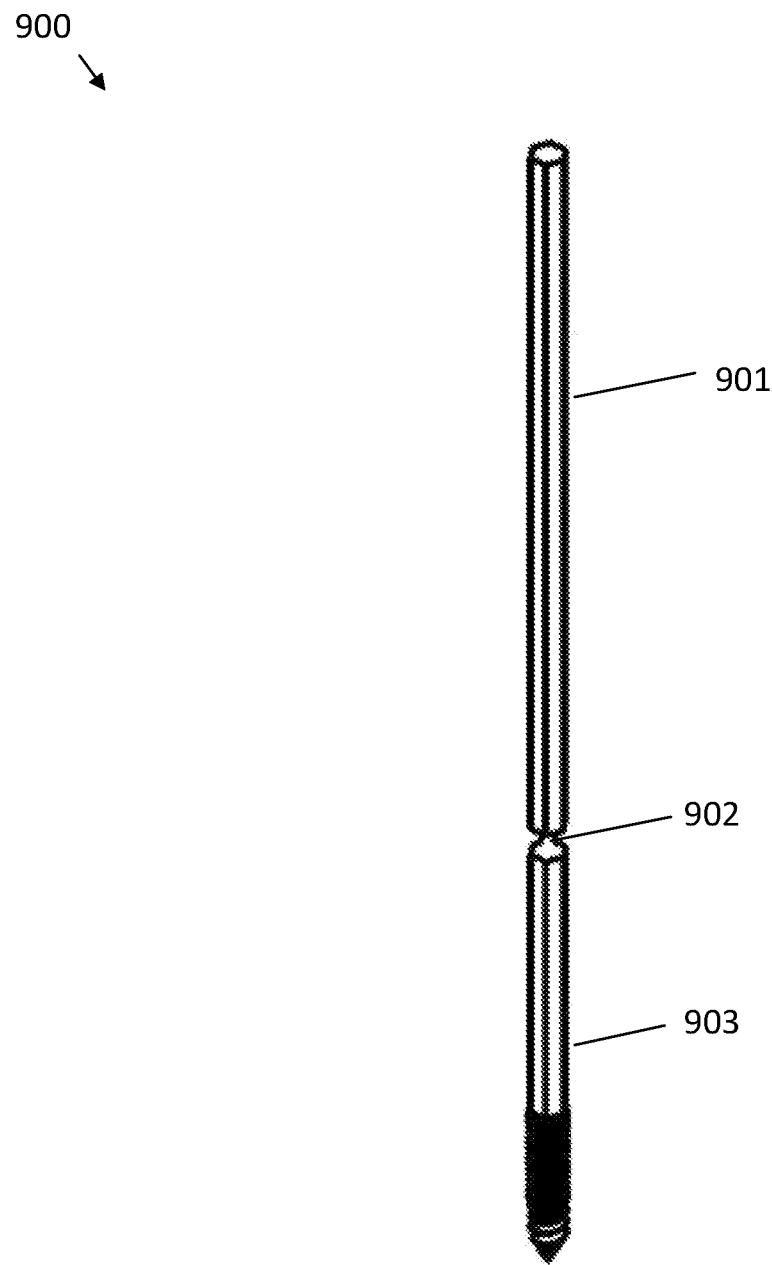
FIG. 9A is a perspective view of another embodiment of a guiding device.
Figure 9B:
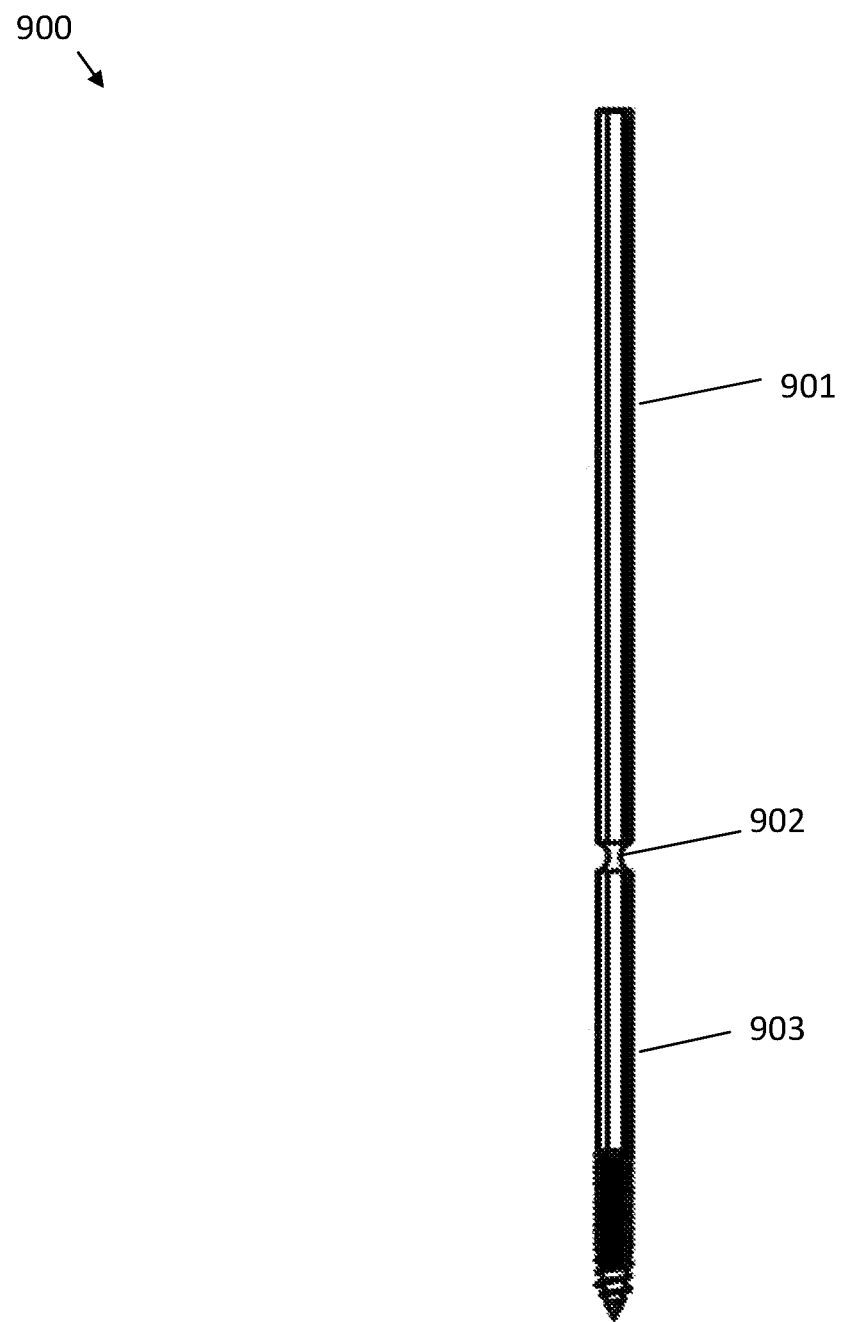
FIG. 9B is a front view of the guiding device of FIG. 9A.

FIG. 9A is a perspective view of the embodiment of a hexagonal guiding device 900, which has a rod 901 and a guide pin 903 that are releasably coupled by an intermediate portion 902. The helical cross section allows the guide pin 903 to engage with a tool such as a drill for subsequent retrieval and removal of the guide pin 903 after a therapeutic bone plan has been inserted. It is contemplated that other cross-sectional shapes (e.g., non-circular shapes) can be used that mate with a tool. FIG. 9B is a frontal view of guiding device 900.

Figure 10A:
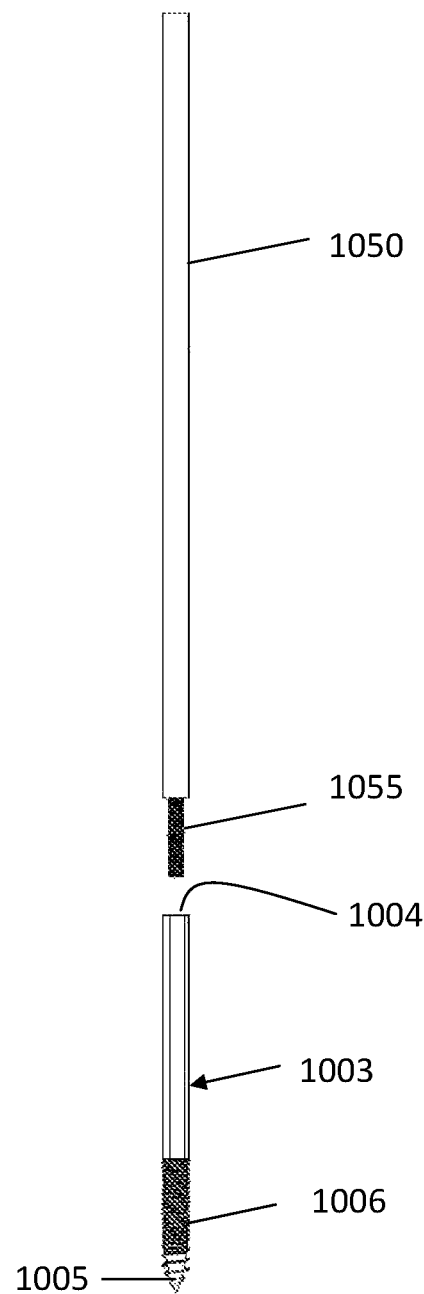
FIG. 10A is a front view of another embodiment of a guide pin and a screwdriver for removing the guide pin.
Figure 10B:
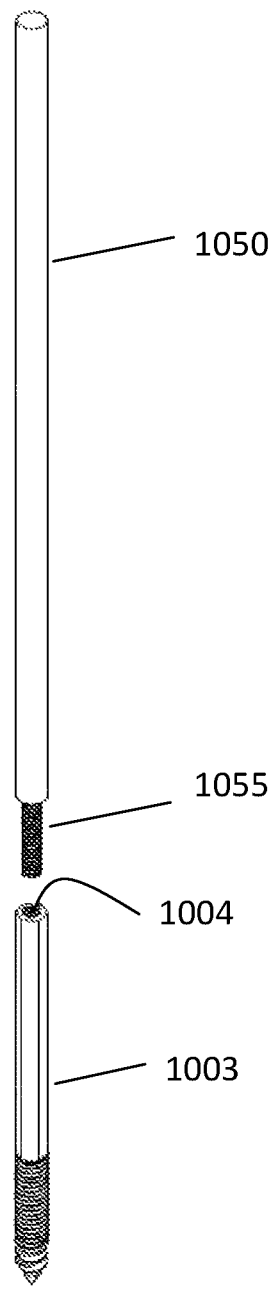
FIG. 10B is a perspective view of the guide pin and screwdriver of FIG. 10A.

FIG. 10A is a frontal view of a guide pin 1003, which has an internal threaded portion 1004 that engages with an external threaded portion 1055 of screwdriver 1050. Internal threaded portion 1004 is threaded in the same direction as the external threads on the body 1006 and the tip 1005 of guide pin 1003. In this manner, the external threads of guide pin 1003 can be screwed into the spinal vertebra 720 in a first direction (e.g., clockwise), while external threads 1055 of screwdriver 1050 can be screwed into internal threaded portion 1004 of guide pin 1003 in an opposite direction (e.g., counter-clockwise) to remove guide pin 1003 from the spinal vertebra 720. FIG. 10B is a perspective view of the guide pin 1003 providing a better view into the internal threaded portion 1004.

Figure 11A:
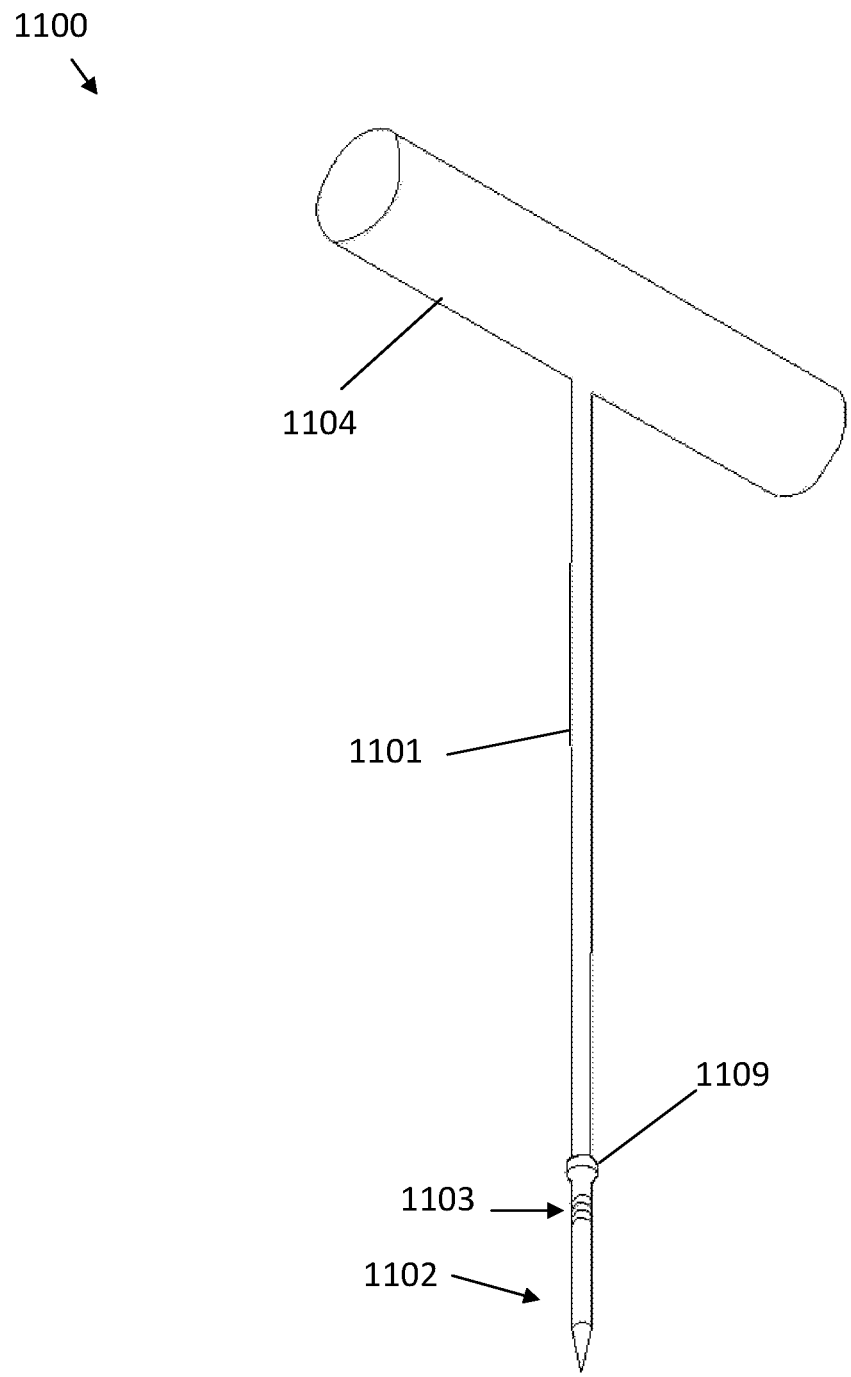
FIG. 11A is a perspective view of another embodiment of a guiding device.
Figure 11B:
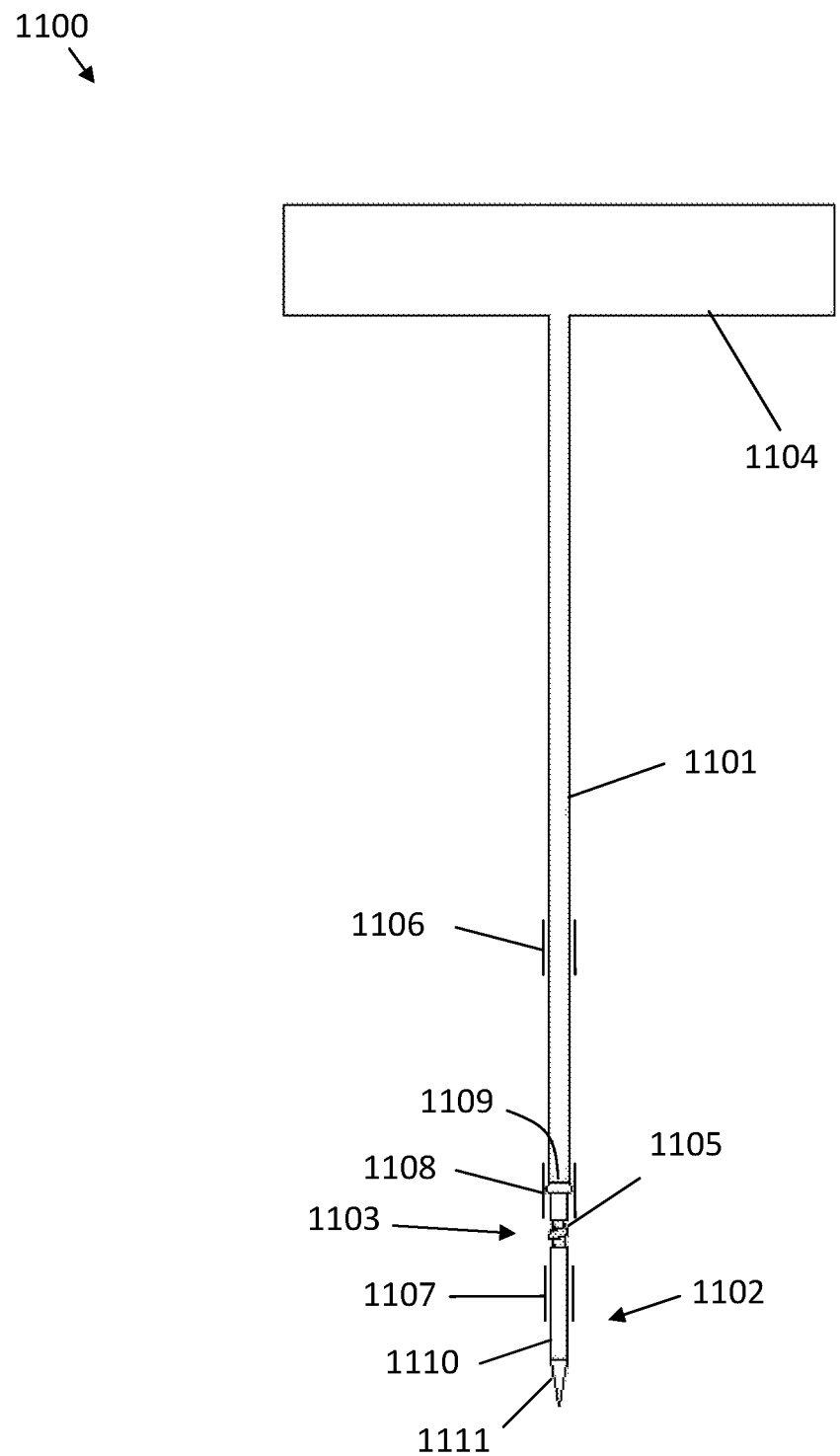
FIG. 11B is a front view of the guiding device of FIG. 11A.

FIGS. 11A-11B show an embodiment of a guiding device 1100 having a rod 1101 and a guide pin 1102. Rod 1101 is releasably coupled to guide pin 1102. It is contemplated that guidance device 1100 comprises an intermediate portion 1103 that connects rod 1101 and guide pin 1102. Intermediate portion 1103 can comprise grooves 1105 as shown in FIGS. 11A-11B that create a break in intermediate portion 1103 to thereby separate rod 1101 from guide pin 1102. Guiding device 1100 further comprises a handle 1104 coupled to rod 1101. Similar to other embodiments, guide pin 1102 comprises a body 1110 and tip 1111.

Guiding device 1100 can further comprise a widened portion 1109 that serves as a safety mechanism by limiting the depth of penetration of guiding device 1100 and preventing further penetration once the widened portion 1109 contacts the bone. As shown in FIGS. 11A-11B, widened portion 1109 can be disposed on rod 1101. However, it is contemplated that widened portion 1109 can be disposed on guide pin 1102. It should be appreciated that widened portion 1109 helps an operator to insert guide pin 1102 at an intended penetration depth by utilizing image guidance to visualize the distance between widened portion 1109 and the surface of the target bone.

Widened portion 1109 can comprise a diameter 1108 that is larger than a diameter 1106 of rod 1101 and a diameter 1107 of body 1110 of guide pin 1102. It should be appreciated that the changed in width between diameter 1106 of rod 1101 and diameter 1108 of widened portion 1109 can be abrupt to thereby form a shoulder that prevents further penetration of the guide pin 1102 once widened portion 1108 contacts the bone. When utilized appropriately, the depth to which the guide pin 1102 is implanted into a bone tissue is no greater than the distance between the sharp end of tip 1111 and intermediate portion 1103.

In embodiments having widened portion 1109 on guide pin 1102, it is contemplated that the width change between diameter 1107 of body 1110 and diameter 1108 of widened portion 1109 can be abrupt to thereby form a shoulder that prevents further penetration of the guide pin 1102 once widened portion 1108 contacts the bone. Thus, the guide pin 1102 can only be driven to a position below intermediate portion 1103 before it is prevented from further penetration by a shoulder on guide pin 1102.

Figure 12A:
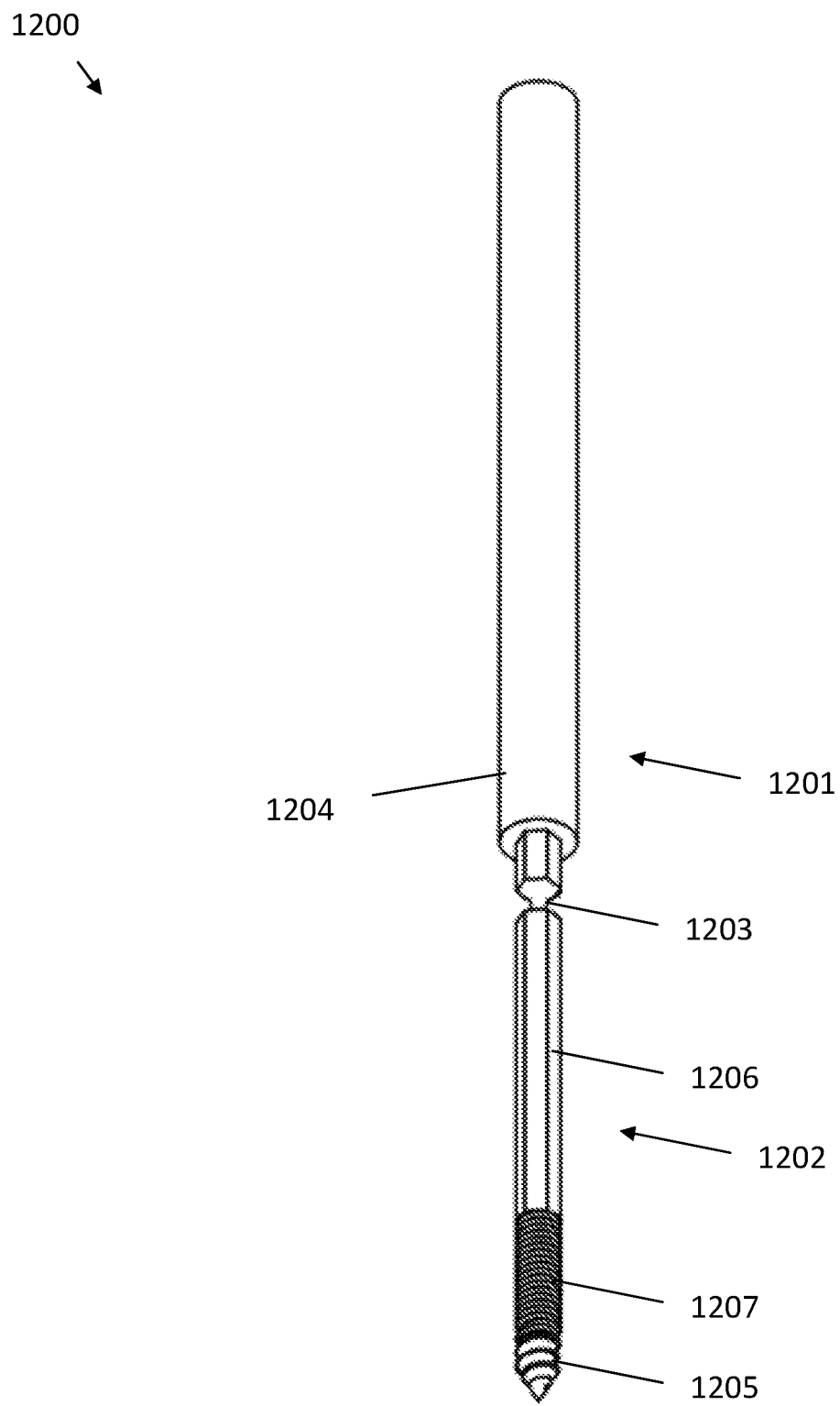
FIG. 12A is a perspective view of another embodiment of a guiding device.
Figure 12B:
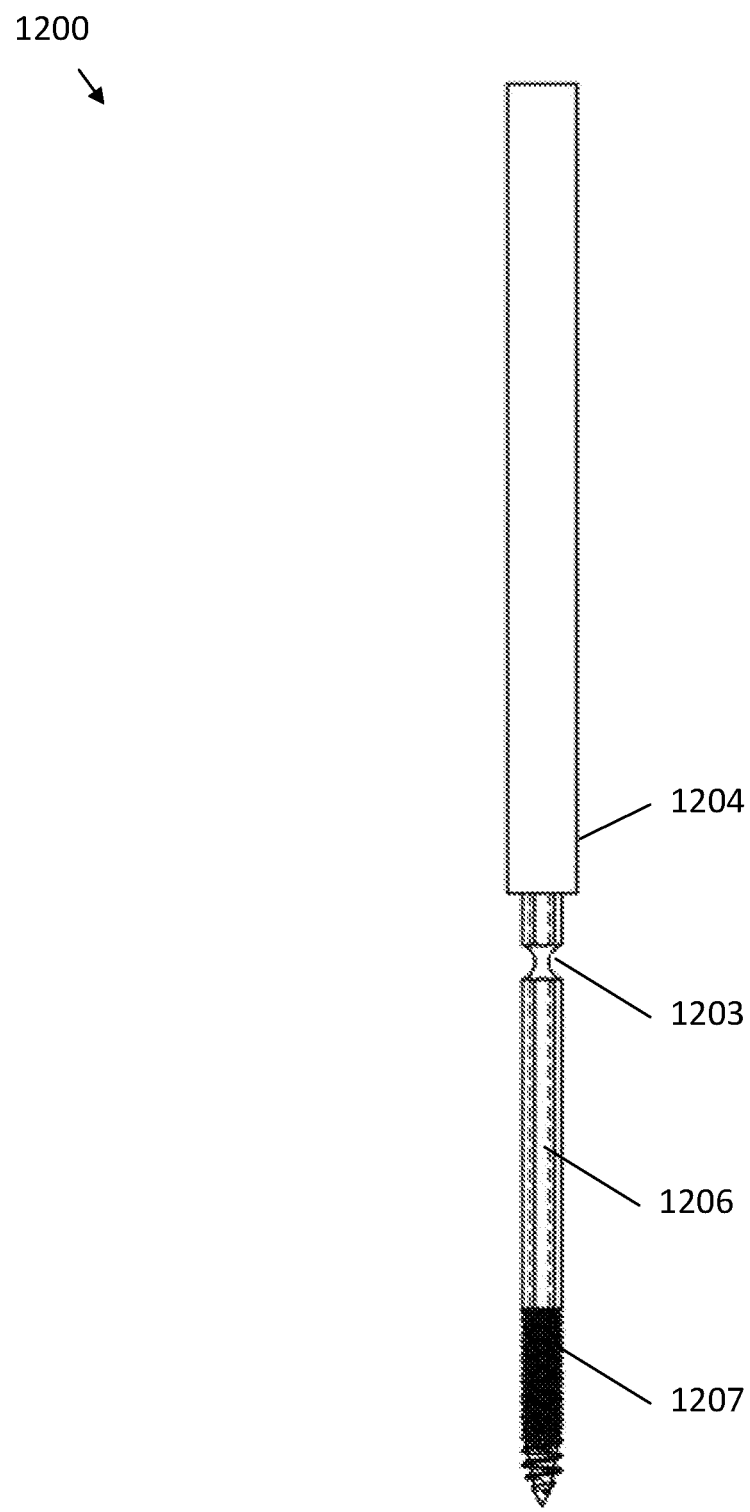
FIG. 12B is a front view with partial hidden lines view of the guiding device of FIG. 12A.

FIGS. 12A-12B show another embodiment of a guiding device 1200 having a widened portion 1204 on a rod 1201 that is releasably coupled to a guide pin 1202. Widened portion 1204 acts as a safety mechanism to prevent guide pin 1202 from advancing into bone beyond widened portion 1204. Once the sharp end of a tip 1205 of guide pin 1202 touches the bone surface at an appropriate entry site, an operator can apply a force to advance guide pin 1202 into an implantation site followed by a breakaway bending or side-to-side hammering of rod 1201 to separate the guide pin 1202 so that guide pin 1202 can act as a guide for subsequent placement of a surgical device (e.g., a surgical screw). A pre-defined limit of penetration of guide pin 1202 into bone is achieved by widened portion 1204 of rod 1201. Similar to widened portion 1108 of guiding device 1100, the abrupt transition from the larger diameter of widened portion 1204 to lower diameter of rod creates a shoulder that signals to a radiologist or surgeon to stop the drilling of guide pin 1202 and withdraw guiding device 1200 so as to expose an intermediate portion 1203 designed to break to separate rod 1201 from guide pin 1202.

Guide pin 1202 comprises a non-threaded body portion 1206 and a threaded body portion 1207. Additionally, or alternatively, the cross-sectional area of non-threaded body portion 1206 has a hexagonal shape that is sized and dimensioned to mate with a tool to counter-rotate guide pin 1202 for extraction after the surgical device has been implanted. It is contemplated that other shapes can be used that mate with a tool to extract guide pin 1202. Unlike widened portion 1108 in guiding device 1100, widened portion 1204 extends from a pre-determined location to an end of rod 1201. It is contemplated that a larger area of widened portion 1204 provides additional image guidance to visualize the distance between widened portion 1204 and the surface of the target bone. Guiding device 1200 can be mated with a drill to drive guiding device 1200 into a bone, or otherwise can further comprise a handle to assist in driving guiding device 1200 into the bone.

Figure 13:
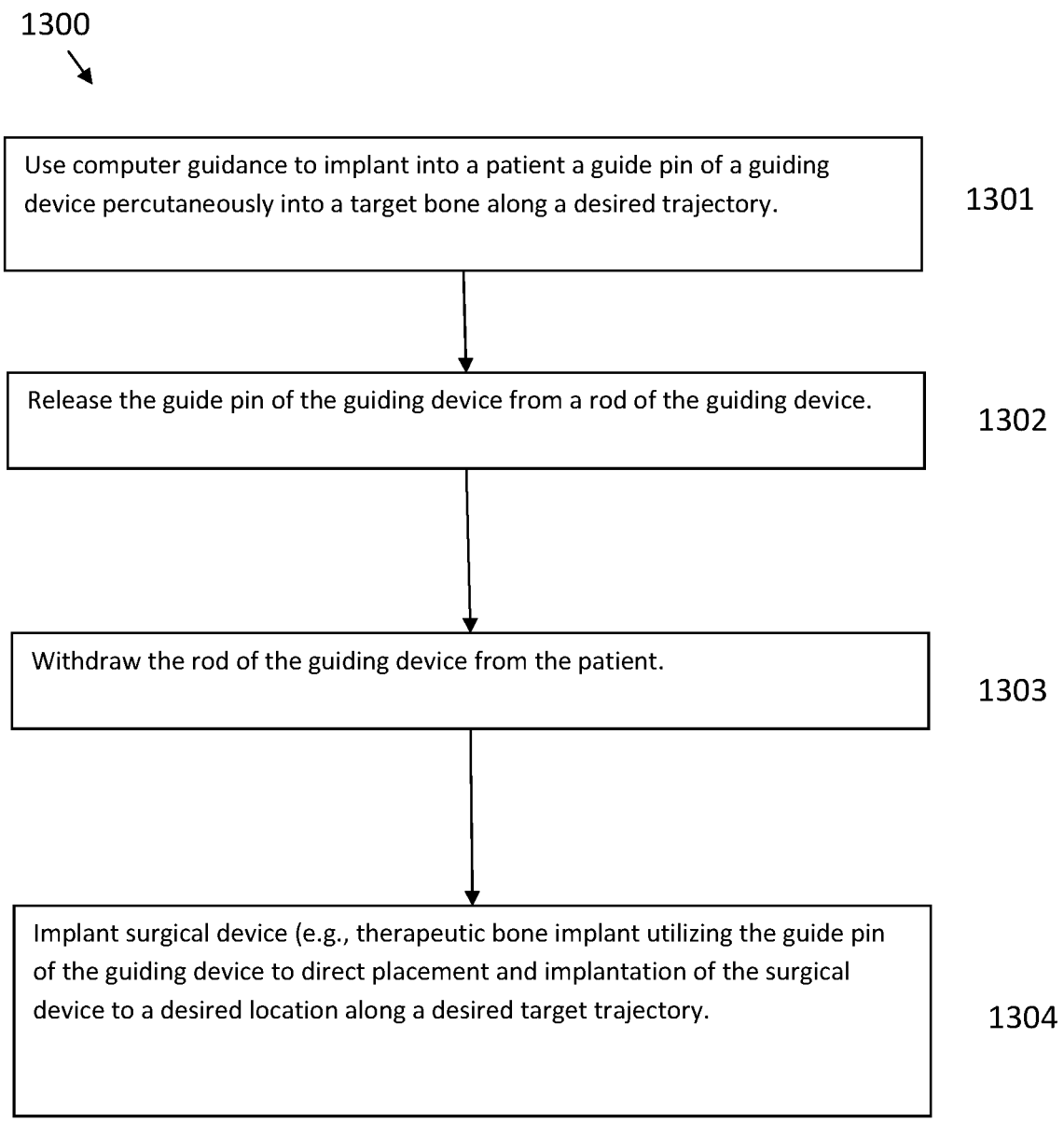
FIG. 13 is a flowchart of an exemplary method of implanting a guiding device.

FIG. 13 shows a flowchart that depicts an exemplary method of implanting a guide pin. A contemplated method comprises a step of using imaging guidance to implant a guide pin of a guiding device (e.g., guiding device 100, 200, 300, 1100, 1200, etc.) into a target bone along a desired trajectory 1301. It is contemplated that the guiding device can be driven into a target bone by one or more of (i) coupling the guidance device to a drill and drilling the guidance device into the target bone, (ii) pushing guiding device into a target bone, and (iii) hammering an end of guiding device to thereby drive the guiding device into the target bone. It is contemplated that at least a portion of the guide pin protrudes from the bone to allow a radiologist or surgeon to visually find the guide pin.

The method further comprises a step of detaching the rod from the guide pin to thereby leave the guide pin implanted in the target bone 1302. Detachment of the rod from the guide pin can be performed by one or more of (i) moving the rod side to side and/or back and forth relative to the guide pin embedded in the target bone to thereby break an intermediate portion, (ii) unmating a threaded or other fastener connection between the rod and the guide pin embedded in the target bone to thereby separate the rod from the guide pin, and (iii) bending the rod relative to the guide pin embedded in the target bone to cause a break in an intermediate portion between the rod and the guide pin.

The method further comprises a step of withdrawing the rod from the patient 1303. This will also include withdrawing tools used to drive the guiding device into the target bone (e.g., a drill) or also withdrawing a handle that is connected to the rod. A surgical device is then implanted utilizing the guide pin embedded in the target bone to direct placement of the surgical device along a desired location and trajectory 1304. For example, a cannulated pedicle screw is driven into the target bone, such that the screw is driven over the guide pin. In some embodiments, the guide pin is driven into the bone at a shorter depth compared to the surgical device.

It is contemplated that the guide pin can be subsequently removed from the bone. The guide pin can mate with a tool (e.g., drill, screwdriver) to rotate and unscrew guide pin from the bone. For example, the guide pin can comprise a specific cross-sectional area (e.g., hexagonal) that allows it to mate with a tool for removal. In another embodiment, the guide pin can comprise threads that mate with threads from a tool to allow the guide pin to be rotates out of the bone.

It is contemplated that the diameter ranges and lengths for rod and body of guide pin described in guiding devices 100 and 200 are applicable to rod and body of guide pins of guide pins of the other guiding devices described herein (e.g., guiding device 300, 900, 1000, 1100, etc.).

It should be appreciated that a robotic device can be used to implant a surgical device into bone with use of a guide pin to help the robotic device navigate the surgical device into the target bone. Additionally, or alternatively, a robotic device can be used to place a guide pin into a target bone for its subsequent use to guide a surgical device (e.g., therapeutic bone implant). A computer may be used to place a guide pin into a target pin for its subsequent use to guide a surgical device (e.g., therapeutic bone implant). Additionally, or alternatively, a computer can be used to implant a surgical device (e.g., therapeutic implant) into bone with use of a guide pin to help navigate the surgical device into the target bone.

It is contemplated guiding devices described herein (e.g., guiding device 100, 200, 300, 1100, etc.) can be molded as a single, unitary piece (i.e., they are manufactured as a single piece and not of separate units that are thereafter connected to one another). The construction details of guiding devices described herein (e.g., guiding device 100, 200, 300, 1100, etc.) can have one or more of a guide pin, rod, and an intermediate portion made of metal or any sufficiently rigid and strong material such as high-strength plastic and the like or any combination thereof. It is contemplated that the guide pin of guiding devices described herein (e.g., guiding device 100, 200, 300, 1100, etc.) can comprise a ferromagnetic or radioactive material.

The guiding devices described herein (e.g., guiding device 100, 200, 300, 1100, etc.) may be constructed by one or more methods chosen from: three-dimensional printing; digital sculpting; CNC routing; stereolithography; utilization of a pre-fabricated mold; robotic, machine, or manual sculpting of component materials. There is more latitude in choosing materials for construction of guiding devices than in choosing materials for the therapeutic bone screws or other surgical devices which the guide pin of the guiding devices guides since (i) there is only a limited bone interface with the guide pin and (ii) the guide pin does not have a primary structural support function.

It should be appreciated that a guiding device can be used to drive a guide pin into one or more target bones. Additionally, or alternatively, one or more guiding devices can be placed within the same or multiple bones prior to implantation of a surgical device.

It should further be appreciated that guiding devices provide a firm and accurate guidance of a pedicle screw or other surgical devices in the bone due to the rigid nature of the guiding device and guide pin. In prior art, guide wires with flexible distal ends are routinely used for surgeries but due to the hard nature of the bone tissue, flexible or flimsy guide wires may become misdirected. Moreover, a flexible or flimsy guide wire does not allow a calibrated breaking point mechanism due to inherent flexibility present in the guide wire material. The guiding devices with a detachable guide pin, due to its rigidity and hardness, allows deployment at a fixed pre-defined location and allows subsequent advancement of a pedicle screw or other surgical device over it, thereby solving at least two major shortcomings present in the prior art.

Although intermediate portion in many of the guiding devices described herein have notches or grooves, it is contemplated that the rod and guide pin can be detachably fastened by means of a mechanism chosen from the following: friction, a snapping mechanism, a male-female mating connection, screwing, adhesive, putty, magnetism.

In other contemplated embodiments, a mechanism to engage an end of a guide pin with a driver so that the guide pin can be subsequently removed after it has been used to guide a therapeutic bone graft or other surgical device is contemplated.

The present invention describes guiding devices with a detachable guide pin which permits placement of an implanted guide pin which may be placed in a radiology suite, and used for subsequent placement of a cannulated pedicle screw or other surgical device optionally occurring at a different venue (e.g., operating theater) than said placement of said implanted guide; also, said subsequent placement of a cannulated pedicle screw may optionally occur on a different day than said placement of said implanted guide.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A guiding device for guiding a hollow surgical device into a bone of a patient, comprising:
   a rod having a first end, a second end, and a widened portion between the first and second ends;
   a guide pin releasably coupled to the second end of the rod;
   wherein the guide pin comprises (i) a tapered portion that tapers inwardly to thereby form a tip for driving the guide pin into the bone, and (ii) a first body portion having a width;
   wherein the rod has (i) a first diameter from the first end to the widened portion and from the second end to the widened portion, and (ii) a second diameter at the widened portion; and
   wherein the second diameter is larger than the first diameter.

2. The device of claim 1, wherein the rod and guide pin are releasably coupled by an intermediate portion that (1) connects the rod and guide pin, and (2) comprises a diameter that is smaller than the first diameter of the rod to thereby allow the intermediate portion to break and separate the rod from the guide pin.

3. The device of claim 1, wherein the guide pin comprises a non-circular cross section.

4. The device of claim 1, wherein the widened portion is proximal to the first end of the rod and distal to the second end of the rod.

5. The device of claim 1, further comprising a handle disposed on the second end of the rod, and wherein the handle and the rod form a T shape.

6. The device of claim 1, wherein the width of the body of the guide pin is less than 3.5 mm.

7. The device of claim 1, wherein the guide pin comprises a ferromagnetic or radioactive material.

* * * * *